United States Patent
Picard et al.

(10) Patent No.: US 6,656,932 B2
(45) Date of Patent: Dec. 2, 2003

(54) BENZO THIADIAZINE MATRIX METALLOPROTEINASE INHIBITORS

(75) Inventors: Joseph Armand Picard, Canton, MI (US); Michael William Wilson, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/074,646

(22) Filed: Feb. 13, 2002

(65) Prior Publication Data

US 2002/0156069 A1 Oct. 24, 2002

Related U.S. Application Data

(60) Provisional application No. 60/268,782, filed on Feb. 14, 2001.

(51) Int. Cl.$^7$ .................. C07D 285/22; C07D 285/24; A61K 31/5415
(52) U.S. Cl. ................. 514/223.2; 514/222.8; 514/219.05; 514/211.15; 514/211.08; 514/212.08; 544/12; 544/13; 540/599
(58) Field of Search ............... 544/12, 13; 540/599; 514/223.2, 222.8, 217.05, 211.15, 211.08, 212.08

(56) References Cited

FOREIGN PATENT DOCUMENTS

| EP | 0935963 | 8/1999 |
|---|---|---|
| EP | 1138680 | 10/2001 |
| FR | 4279 M | 8/1966 |
| WO | WO 97/49692 A | 12/1997 |
| WO | WO 98/49146 A | 11/1998 |
| WO | WO 01/09485 | 2/2000 |
| WO | WO 01/12611 | 2/2001 |
| WO | WO 01/63244 A1 | 8/2001 |
| WO | WO 02/34726 | 5/2002 |
| WO | WO 02/34753 | 5/2002 |
| WO | WO 02/064080 | 8/2002 |

OTHER PUBLICATIONS

Montana, John, et al, "The design of selective non–substrate–based matrix metalloproteinase inhibitors", Current Opinion in Drug Discovery & Development, 2000; 3(4), pp. 353–361.

Clark, Ian, et al, "Matrix metalloproteinase inhibitors in the treatment of arthritis", Current Opinions in Anti–inflammatory & Immunomodulatory Investigational Drugs, 2000; 2(1), pp. 16–25.

Chen, James, et al, "Structure–Based Design of a Novel, Potent, and Selective Inhibitor for MMP–13 Utilizing NMR Spectroscopy and Computer–Aided Molecular Design", J. Am. Chem. Soc., 2000, 122; pp. 9648–9654.

*Primary Examiner*—John M. Ford
(74) *Attorney, Agent, or Firm*—Charles W. Ashbrook; Claude F. Purchase, J

(57) ABSTRACT

Selective MMP-13 inhibitors are benzo thiadiazines of the Formula

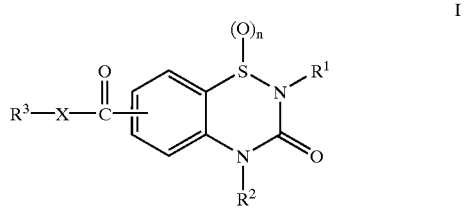

or a pharmaceutically acceptable salt thereof, wherein $R^2$ is hydrogen or alkyl; $R^1$ and $R^3$ include hydrogen, alkyl, and aryl, with the proviso that $R^3$ is not $(CH_2)_m$ biphenyl or $(CH_2)_m$ substituted biphenyl; X is O or NH, n is 0, 1, or 2. The compounds of Formula I, or a pharmaceutically acceptable salt thereof, is useful for treating diseases mediated by an MMP-13 enzyme, including diseases selected from osteoarthritis, rheumatoid arthritis, cancer, inflammation, and heart failure.

16 Claims, No Drawings

BENZO THIADIAZINE MATRIX METALLOPROTEINASE INHIBITORS

CROSS-REFERENCE TO RELATED APPLICATIONS

This application claims benefit of priority from U.S. provisional application No. 60/268,782, filed Feb. 14, 2001.

FIELD OF THE INVENTION

This invention relates to a group of benzo thiadiazine derivatives which inhibit matrix metalloproteinase enzymes, and thus are useful for treating diseases resulting from tissue breakdown, such as heart disease, multiple sclerosis, arthritis, atherosclerosis, and osteoporosis.

BACKGROUND OF THE INVENTION

Matrix metalloproteinases (sometimes referred to as MMPs) are naturally occurring enzymes found in most mammals. Over-expression and activation of MMPs or an imbalance between MMPs and inhibitors of MMPs have been suggested as factors in the pathogenesis of diseases characterized by the breakdown of extracellular matrix or connective tissues.

Stromelysin-1 and gelatinase A are members of the matrix metalloproteinases (MMP) family. Other members include fibroblast collagenase (MMP-1), neutrophil collagenase (MMP-8), gelatinase B (92 kDa gelatinase) (MMP-9), stromelysin-2 (MMP-10), stromelysin-3 (MMP-11), matrilysin (MMP-7), collagenase 3 (MMP-13), TNF-alpha converting enzyme (TACE), and other newly discovered membrane-associated matrix metalloproteinases (Sato H., Takino T., Okada Y., Cao J., Shinagawa A., Yamamoto E., and Seiki M., Nature, 1994;370:61–65). These enzymes have been implicated with a number of diseases which result from breakdown of connective tissue, including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, and tumor metastasis. A method for preventing and treating these and other diseases is now recognized to be by inhibiting metalloproteinase enzymes, thereby curtailing and/or eliminating the breakdown of connective tissues that results in the disease states.

The catalytic zinc in matrix metalloproteinases is typically the focal point for inhibitor design. The modification of substrates by introducing zinc chelating groups has generated potent inhibitors such as peptide hydroxamates and thiol-containing peptides. Peptide hydroxamates and the natural endogenous inhibitors of MMPs (TIMPs) have been used successfully to treat animal models of cancer and inflammation. MMP inhibitors have also been used to prevent and treat congestive heart failure and other cardiovascular diseases, U.S. Pat. No. 5,948,780.

A major limitation on the use of currently known MMP inhibitors is their lack of specificity for any particular enzyme. Recent data has established that specific MMP enzymes are associated with some diseases, with no effect on others. The MMPs are generally categorized based on their substrate specificity, and indeed the collagenase subfamily of MMP-1, MMP-8, and MMP-13 selectively cleave native interstitial collagens, and thus are associated only with diseases linked to such interstitial collagen tissue. This is evidenced by the recent discovery that MMP-13 alone is over expressed in breast carcinoma, while MMP-1 alone is over expressed in papillary carcinoma (see Chen et al., J. Am. Chem. Soc., 2000;122:9648–9654).

There appears to be few selective inhibitors of MMP-13 reported. A compound named WAY-170523 has been reported by Chen et al., supra., 2000, and a few other compounds are reported in PCT international application publication number WO 01/63244 A1, as allegedly selective inhibitors of MMP-13. Further, U.S. Pat. No. 6,008,243 discloses inhibitors of MMP-13. However, no selective or nonselective inhibitor of MMP-13 has been approved and marketed for the treatment of any disease in any mammal. Accordingly, the need continues to find new low molecular weight compounds that are potent and selective MMP inhibitors, and that have an acceptable therapeutic index of toxicity/potency to make them amenable for use clinically in the prevention and treatment of the associated disease states. An object of this invention is to provide a group of selective MMP-13 inhibitor compounds characterized as being benzo thiadiazines.

SUMMARY OF THE INVENTION

This invention provides a group of benzo thiadiazine compounds that are inhibitors of matrix metalloproteinase enzymes, and especially MMP-13. The invention is more particularly directed to compounds defined by Formula I

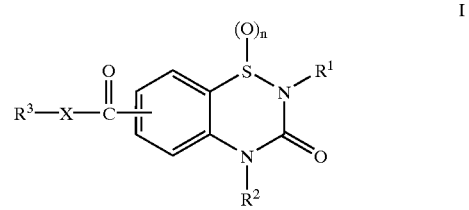

or a pharmaceutically acceptable salt thereof, wherein:

n is 0, 1, or 2;

X is O or NH;

$R^2$ is H, $C_1$–$C_6$ alkyl, or $C_1$–$C_6$ substituted alkyl;

$R^1$ and $R^3$ independently are H, acyl, substituted acyl, $C_1$–$C_6$ alkyl, $C_1$–$C_6$ substituted alkyl, $C_2$–$C_6$ alkenyl, $C_2$–$C_6$ substituted alkenyl, $C_2$–$C_6$ alkynyl, $C_1$ $C_6$ substituted alkynyl, $(CH_2)_m$ aryl, $(CH_2)_m$ substituted aryl, $(CH_2)_m$ heteroaryl, $(CH_2)_m$ substituted heteroaryl, $(CH_2)_m$ cycloalkyl, or $(CH_2)_m$ substituted cycloalkyl; and each m independently is an integer of from 0 to 6, with the proviso that $R^3$ is not $(CH_2)_m$ biphenyl or $(CH_2)_m$ substituted biphenyl.

Another invention embodiment are compounds of Formula I, or a pharmaceutically acceptable salt thereof, wherein $R^1$ and $R^3$ are not both selected from H or $C_1$–$C_6$ alkyl.

Another invention embodiment are compounds of Formula I, or a pharmaceutically acceptable salt thereof, wherein $R^3$ is not acyl or substituted acyl when X is O.

Another invention embodiment are compounds of Formula I, or a pharmaceutically acceptable salt thereof, wherein each m is 1.

Another invention embodiment are compounds of Formula II

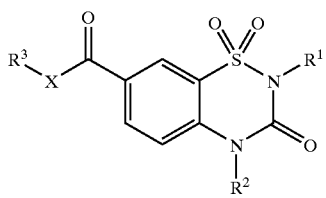

II or a pharmaceutically acceptable salt thereof, wherein $R^1$, $R^2$, $R^3$, and X are as defined above.

Another invention embodiment are compounds of Formulas I or II, or a pharmaceutically acceptable salt thereof, wherein $R_2$ is H, alkyl or substituted alkyl, and $R^1$ and $R^3$ independently are $(CH_2)_m$ phenyl, $(CH_2)_m$ heteroaryl, $(CH_2)_m$ cycloalkyl, $C_2$–$C_6$ alkenyl, or $C_2$–$C_6$ substituted alkenyl, wherein phenyl, heteroaryl, and cycloalkyl may be unsubstituted or substituted.

Another invention embodiment are compounds of Formulas I or II, or a pharmaceutically acceptable salt thereof, wherein $R^2$ is hydrogen or $C_1$–$C_6$ alkyl, and $R^1$ and $R^3$ independently are $C_1$–$C_6$ substituted alkyl, wherein at least one substituent is an aryl group such as phenyl or substituted phenyl.

Another invention embodiment is a compound of Formula I, or a pharmaceutically acceptable salt thereof, selected from:

2-Benzyl-4-methyl-1,1,3-trioxo-1,2,3,4-tetrahydro-1l$^6$-benzo[1,2,4]thiadiazine-7-carboxylic acid benzyl ester;

2-Benzyl-4-methyl-1,1,3-trioxo-1,2,3,4-tetrahydro-1l$^6$-benzo[1,2,4]thiadiazine-7-carboxylic acid benzylamide;

2-Benzyl-4-methyl-1,1,3-trioxo-1,2,3,4-tetrahydro-1l$^6$-benzo[1,2,4]thiadiazine-7-carboxylic acid (pyridin-4-ylmethyl)-amide;

2-Benzyl-4-methyl-1,1,3-trioxo-1,2,3,4-tetrahydro-1l$^6$-benzo[1,2,4]thiadiazine-7-carboxylic acid (1H-indol-5-ylmethyl)-amide;

2-Benzyl-4-methyl-1,1,3-trioxo-1,2,3,4-tetrahydro-1l$^6$-benzo[1,2,4]thiadiazine-7-carboxylic acid 4-methoxy-benzylamide;

2-Benzyl-4-methyl-1,1,3-trioxo-1,2,3,4-tetrahydro-1l$^6$-benzo[1,2,4]thiadiazine-7-carboxylic acid 4-(2-tert-butylsulfamoyl-ethyl)-benzylamide;

2-Benzyl-4-methyl-1,1,3-trioxo-1,2,3,4-tetrahydro-1l$^6$-benzo[1,2,4]thiadiazine-7-carboxylic acid (1H-indol-2-ylmethyl)-amide;

2-Benzyl-4-methyl-1,1,3-trioxo-1,2,3,4-tetrahydro-1l$^6$-benzo[1,2,4]thiadiazine-7-carboxylic acid 4-(2-sulfamoyl-ethyl)-benzylamide;

2-(4-Methanesulfonyl-benzyl)-4-methyl-1,1,3-trioxo-1,2,3,4-tetrahydro-1l$^6$-benzo[1,2,3,4]thiadiazine-7-carboxylic acid benzylamide;

4-(7-Benzylcarbamoyl-4-methyl-1,1,3-trioxo-3,4-dihydro-1H-1l$^6$-benzo[1,2,4]thiadiazin-2-ylmethyl)-benzoic acid tert-butyl ester;

4-(7-Benzylcarbamoyl-4-methyl-1,1,3-trioxo-3,4-dihydro-1H-1l$^6$-benzo[1,2,4]thiadiazin-2-ylmethyl)-benzoic acid;

4-[7-(4-Methoxy-benzylcarbamoyl)-4-methyl-1,1,3-trioxo-3,4-dihydro-1H-1l$^6$-benzo[1,2,3,4]thiadiazin-2-ylmethyl]-benzoic acid tert-butyl ester;

4-[7-(4-Methoxy-benzylcarbamoyl)-4-methyl-1,1,3-trioxo-3,4-dihydro-1H-1l$^6$-benzo[1,2,4]thiadiazin-2-ylmethyl]-benzoic acid;

2-(4-Carbamoyl-benzyl)-4-methyl-1,1,3-trioxo-1,2,3,4-tetrahydro-1l$^6$-benzo[1,2,4]thiadiazine-7-carboxylic acid 4-methoxy-benzylamide;

2-(4-Methanesulfonyl-benzyl)-4-methyl-1,1,3-trioxo-1,2,3,4-tetrahydro-1l$^6$-benzo[1,2,4]thiadiazine-7-carboxylic acid 4-methoxy-benzylamide;

2-Benzyl-4-methyl-1,1,3-trioxo-1,2,3,4-tetrahydro-1l$^6$-benzo[1,2,4]thiadiazine-7-carboxylic acid 4-fluoro-benzylamide;

4-Methyl-2-(4-nitro-benzyl)-1,1,3-trioxo-1,2,3,4-tetrahydro-1l$^6$-benzo[1,2,4]thiadiazine-7-carboxylic acid 4-methoxy-benzylamide;

4-Methyl-2-(4-methylsulfamoyl-benzyl)-1,1,3-trioxo-1,2,3,4-tetrahydro-1l$^6$-benzo[1,2,4]thiadiazine-7-carboxylic acid 4-methoxy-benzylamide;

4-Methyl-2-[4-(morpholine-4-sulfonyl)-benzyl]-1,1,3-trioxo-1,2,3,4-tetrahydro-1l$^6$-benzo[1,2,3,4]thiadiazine-7-carboxylic acid 4-methoxy-benzylamide;

4-[7-(4-Fluoro-benzylcarbamoyl)4-methyl-1,1,3-trioxo-3,4-dihydro-1H-1l$^6$-benzo[1,2,4]thiadiazin-2-ylmethyl]-benzoic acid methyl ester;

2-Benzyl-4-methyl-1,1,3-trioxo-1,2,3,4-tetrahydro-1l$^6$-benzo[1,2,4]thiadiazine-7-carboxylic acid (2-methoxy-pyridin-4-ylmethyl)-amide;

4-Methyl-2-naphthalen-2-ylmethyl-1,1,3-trioxo-1,2,3,4-tetrahydro-1l$^6$-benzo[1,2,4]thiadiazine-7-carboxylic acid 4-methoxy-benzylamide;

2-Biphenyl-4-ylmethyl-4-methyl-1,1,3-trioxo-1,2,3,4-tetrahydro-1l$^6$-benzo[1,2,4]thiadiazine-7-carboxylic acid 4-methoxy-benzylamide;

2-Benzyl-4-methyl-1,1,3-trioxo-1,2,3,4-tetrahydro-1l$^6$-benzo[1,2,4]thiadiazine-7-carboxylic acid (2,1,3-benzothiadiazol-5-ylmethyl)-amide;

4-[7-(4-Fluoro-benzylcarbamoyl)-4-methyl-1,1,3-trioxo-3,4-dihydro-1H-1l$^6$-benzo[1,2,4]thiadiazin-2-ylmethyl]-benzoic acid;

4-[7-(4-Methoxy-benzylcarbamoyl)-4-methyl-1,1,3-trioxo-3,4-dihydro-1H-1l$^6$-benzo[1,2,4]thiadiazin-2-ylmethyl]-benzoic acid 2-dimethylamino-ethyl ester hydrochloride;

4-Methyl-1,1,3-trioxo-2-[4-(piperidine-1-carbonyl)-benzyl]-1,2,3,4-tetrahydro-1l$^6$-benzo[1,2,4]thiadiazine-7-carboxylic acid 4-methoxy-benzylamide;

2-{4-[7-(4-Methoxy-benzylcarbamoyl)4-methyl-1,1,3-trioxo-3,4-dihydro-1H-1λ$^6$-benzo[1,2,3,4]thiadiazin-2-ylmethyl]-benzoylamino}-3-methyl-butyric acid;

2-(4-Cyano-benzyl)4-methyl-1,1,3-trioxo-1,2,3,4-tetrahydro-1l$^6$-benzo[1,2,3,4]thiadiazine-7-carboxylic acid 4-methoxy-benzylamide;

{4-[7-(4-Methoxy-benzylcarbamoyl)-4-methyl-1,1,3-trioxo-3,4-dihydro-1H-1λ$^6$-benzo[1,2,3,4]thiadiazin-2-ylmethyl]-phenyl }-acetic acid;

4-[7-(3-Methoxy-benzylcarbamoyl)-4-methyl-1,1,3-trioxo-3,4-dihydro-1H-1λ$^6$-benzo[1,2,4]thiadiazin-2-ylmethyl]-benzoic acid;

4-Methyl-1,1,3-trioxo-2-[4-(2H-tetrazol-5-yl)-benzyl]-1,2,3,4-tetrahydro-1λ$^6$-benzo[1,2,4]thiadiazine-7-carboxylic acid 4-methoxy-benzylamide;

2-(4-Amino-benzyl)-4-methyl-1,1,3-trioxo-1,2,3,4-tetrahydro-1l$^6$-benzo[1,2,4]thiadiazine-7-carboxylic acid 4-methoxy-benzylamide;

2-Benzyl-4-methyl-1,1,3-trioxo-1,2,3,4-tetrahydro-1λ$^6$-benzo[1,2,4]thiadiazine-7-carboxylic acid 3-methoxy-benzylamide;

4-Methyl-1,1,3-trioxo-2-pent-2-ynyl-1,2,3,4-tetrahydro-1l$^6$-benzo[1,2,4]thiadiazine-7-carboxylic acid 4-methoxy-benzylamide;

4-Methyl-1,1,3-trioxo-2-(1-phenyl-ethyl)-1,2,3,4-tetrahydro-1l$^6$-benzo[1,2,4]thiadiazine-7-carboxylic acid 4-methoxy-benzylamide;

2-(5-Cyano-pentyl)4-methyl-1,1,3-trioxo-1,2,3,4-tetrahydro-1l$^6$-benzo[1,2,3,4]thiadiazine-7-carboxylic acid 4-methoxy-benzylamide;

2-(E)-But-2-enyl-4-methyl-1,1,3-trioxo-1,2,3,4-tetrahydro-1l$^6$-benzo[1,2,4]thiadiazine-7-carboxylic acid 4-methoxy-benzylamide;

4-Methyl-1,1,3-trioxo-2-(E)-pent-2-enyl-1,2,3,4-tetrahydro-1l$^6$-benzo[1,2,4]thiadiazine-7-carboxylic acid 4-methoxy-benzylamide;

4-Methyl-2-(2-methyl-allyl)-1,1,3-trioxo-1,2,3,4-tetrahydro-1l$^6$-benzo[1,2,4]thiadiazine-7-carboxylic acid 4-methoxy-benzylamide;

4-Methyl-2-(3-methyl-but-2-enyl)-1,1,3-trioxo-1,2,3,4-tetrahydro-1l$^6$-benzo[1,2,4]thiadiazine-7-carboxylic acid 4-methoxy-benzylamide;

4-Methyl-1,1,3-trioxo-2-[2-(toluene-4-sulfonyl)-ethyl]-1,2,3,4-tetrahydro-1l$^6$-benzo[1,2,4]thiadiazine-7-carboxylic acid 4-methoxy-benzylamide;

2-[3-(4-Fluoro-phenyl)-3-oxo-propyl]-4-methyl-1,1,3-trioxo-1,2,3,4-tetrahydro-1l$^6$-benzo[1,2,3,4]thiadiazine-7-carboxylic acid 4-methoxy-benzylamide;

4-Methyl-1,1,3-trioxo-2-{2-[(1-phenyl-methanoyl)-amino]-ethyl}-1,2,3,4-tetrahydro-1l$^6$-benzo[1,2,3,4]thiadiazine-7-carboxylic acid 4-methoxy-benzylamide;

2-Benzo[1,2,5]oxadiazol-5-ylmethyl-4-methyl-1,1,3-trioxo-1,2,3,4-tetrahydro-1l$^6$-benzo[1,2,3,4]thiadiazine-7-carboxylic acid 4-methoxy-benzylamide;

{5-[7-(4-Methoxy-benzylcarbamoyl)-4-methyl-1,1,3-trioxo-3,4-dihydro-1H-1l$^6$-benzo[1,2,3,4]thiadiazin-2-ylmethyl]-isoxazol-3-yl}-carbamic acid methyl ester; and 4-Methyl-1,1,3-trioxo-2-thiazol-4-ylmethyl-1,2,3,4-tetrahydro-1l$^6$-benzo[1,2,4]thiadiazine-7-carboxylic acid 4-methoxy-benzylamide.

Another invention embodiment is a compound selected from:

2-Benzyl-4-methyl-1,1,3-trioxo-1,2,3,4-tetrahydro-1l$^6$-benzo[1,2,4]thiadiazine-7-carboxylic acid (pyridin-3-ylmethyl)-amide;

2-Benzyl-4-methyl-1,1,3-trioxo-1,2,3,4-tetrahydro-1l$^6$-benzo[1,2,4]thiadiazine-7-carboxylic acid 4-methoxy-benzylamide;

2-Benzyl-4-methyl-1,1,3-trioxo-1,2,3,4-tetrahydro-1l$^6$-benzo[1,2,4]thiadiazine-7-carboxylic acid 3-methoxy-benzylamide;

4-(7-Benzylcarbamoyl-4-methyl-1,1,3-trioxo-3,4-dihydro-1H-1l$^6$-benzo[1,2,4]thiadiazin-2-ylmethyl)-benzoic acid tert-butyl ester;

4-(4-Methyl-1,1,3-trioxo-7-[(pyridin-4-ylmethyl)-carbamoyl]-3,4-dihydro-1H-1l$^6$-benzo[1,2,4]thiadiazin-2-ylmethyl)-benzoic acid tert-butyl ester;

4-(4-Methyl-1,1,3-trioxo-7-[(pyridin-3-ylmethyl)-carbamoyl]-3,4-dihydro-1H-1l$^6$-benzo[1,2,3,4]thiadiazin-2-ylmethyl)-benzoic acid tert-butyl ester;

4-[7-(4-Methoxy-benzylcarbamoyl)-4-methyl-1,1,3-trioxo-3,4-dihydro-1H-1l$^6$-benzo[1,2,4]thiadiazin-2-ylmethyl)-benzoic acid tert-butyl ester;

4-[7-(3-Methoxy-benzylcarbamoyl)-4-methyl-1,1,3-trioxo-3,4-dihydro-1 H-1l$^6$-benzo[1,2,3,4]thiadiazin-2-ylmethyl)-benzoic acid tert-butyl ester;

4-(7-Benzylcarbamoyl-4-methyl-1,1,3-trioxo-3,4-dihydro-1H-1l$^6$-benzo[1,2,4]thiadiazin-2-ylmethyl)-benzoic acid;

4-(4-Methyl-1,1,3-trioxo-7-[(pyridin-4-ylmethyl)-carbamoyl]-3,4-dihydro-1H-1l$^6$-benzo[1,2,3,4]thiadiazin-2-ylmethyl)-benzoic acid;

4-(4-Methyl-1,1,3-trioxo-7-[(pyridin-3-ylmethyl)-carbamoyl]-3,4-dihydro-1H-1l$^6$-benzo[1,2,3,4]thiadiazin-2-ylmethyl)-benzoic acid;

4-[7-(4-Methoxy-benzylcarbamoyl)-4-methyl-1,1,3-trioxo-3,4-dihydro-1H-1l$^6$-benzo[1,2,3,4]thiadiazin-2-ylmethyl)-benzoic acid;

4-[7-(3-Methoxy-benzylcarbamoyl)4-methyl-1,1,3-trioxo-3,4-dihydro-1H-1l$^6$-benzo[1,2,3,4]thiadiazin-2-ylmethyl)-benzoic acid;

{4-(7-Benzylcarbamoyl-4-methyl-1,1,3-trioxo-3,4-dihydro-1H-1l$^6$-benzo[1,2,4]thiadiazin-2-ylmethyl)-phenyl}-acetic acid tert-butyl ester;

{4-(4-Methyl-1,1,3-trioxo-7-[(pyridin-4-ylmethyl)-carbamoyl]-3,4-dihydro-1H-1l$^6$-benzo[1,2,3,4]thiadiazin-2-ylmethyl)-phenyl}-acetic acid tert-butyl ester;

{4-(4-Methyl-1,1,3-trioxo-7-[(pyridin-3-ylmethyl)-carbamoyl]-3,4-dihydro-1H-1l$^6$-benzo[1,2,3,4]thiadiazin-2-ylmethyl)-phenyl}-acetic acid tert-butyl ester;

{4-[7-(4-Methoxy-benzylcarbamoyl)-4-methyl-1,1,3-trioxo-3,4-dihydro-1H-1l$^6$-benzo[1,2,4]thiadiazin-2-ylmethyl)-phenyl}-acetic acid tert-butyl ester;

{4-[7-(3-Methoxy-benzylcarbamoyl)-4-methyl-1,1,3-trioxo-3,4-dihydro-1-H-1l$^6$-benzo[1,2,4]thiadiazin-2-ylmethyl)-phenyl}-acetic acid tert-butyl ester;

{4-(7-Benzylcarbamoyl-4-methyl-1,1,3-trioxo-3,4-dihydro-1H-1l$^6$-benzo[1,2,4]thiadiazin-2-ylmethyl)-phenyl}-acetic acid;

{4-(4-Methyl-1,1,3-trioxo-7-[(pyridin-4-ylmethyl)-carbamoyl]-3,4-dihydro-1H-1l$^6$-benzo[1,2,3,4]thiadiazin-2-ylmethyl)-phenyl}-acetic acid;

{4-(4-Methyl-1,1,3-trioxo-7-[(pyridin-3-ylmethyl)-carbamoyl]-3,4-dihydro-1H-1l$^6$-benzo[1,2,3,4]thiadiazin-2-ylmethyl)-phenyl}-acetic acid;

{4-[7-(4-Methoxy-benzylcarbamoyl)4-methyl-1,1,3-trioxo-3,4-dihydro-1H-1l$^6$-benzo[1,2,3,4]thiadiazin-2-ylmethyl)-phenyl}-acetic acid;

{4-[7-(3-Methoxy-benzylcarbamoyl)-4-methyl-1,1,3-trioxo-3,4-dihydro-1H-1l$^6$-benzo[1,2,3,4]thiadiazin-2-ylmethyl)-phenyl}-acetic acid;

2-(4-Methanesulfonyl-benzyl)-4-methyl-1,1,3-trioxo-1,2,3,4-tetrahydro-1l$^6$-benzo[1,2,4]thiadiazine-7-carboxylic acid benzylamide;

2-(4-Methanesulfonyl-benzyl)-4-methyl-1,1,3-trioxo-1,2,3,4-tetrahydro-1l$^6$-benzo[1,2,3,4]thiadiazine-7-carboxylic acid (pyridin-4-ylmethyl)-amide;

2-(4-Methanesulfonyl-benzyl)-4-methyl-1,1,3-trioxo-1,2,3,4-tetrahydro-1l$^6$-benzo[1,2,4]thiadiazine-7-carboxylic acid (pyridin-3-ylmethyl)-amide;

2-(4-Methanesulfonyl-benzyl)4-methyl-1,1,3-trioxo-1,2,3,4-tetrahydro-1l$^6$-benzo[1,2,4]thiadiazine-7-carboxylic acid 4-methoxy-benzylamide;

2-(4-Methanesulfonyl-benzyl)4-methyl-1,1,3-trioxo-1,2,3,4-tetrahydro-1l$^6$-benzo[1,2,4]thiadiazine-7-carboxylic acid 3-methoxy-benzylamide;

4-Methyl-2-(4-methylsulfamoyl-benzyl)-1,1,3-trioxo-1,2,3,4-tetrahydro-1l$^6$-benzo[1,2,4]thiadiazine-7-carboxylic acid benzylamide;

4-Methyl-2-(4-methylsulfamoyl-benzyl)-1,1,3-trioxo-1,
  2,3,4-tetrahydro-1l$^6$-benzo[1,2,4]thiadiazine-7-
  carboxylic acid (pyridin-4-ylmethyl)-amide;

4-Methyl-2-(4-methylsulfamoyl-benzyl)-1,1,3-trioxo-1,
  2,3,4-tetrahydro-1l$^6$-benzo[1,2,4]thiadiazine-7-
  carboxylic acid (pyridin-3-ylmethyl)-amide;

4-Methyl-2-(4-methylsulfamoyl-benzyl)-1,1,3-trioxo-1,
  2,3,4-tetrahydro-1l$^6$-benzo[1,2,4]thiadiazine-7-
  carboxylic acid 4-methoxy-benzylamide;

4-Methyl-2-(4-methylsulfamoyl-benzyl)-1,1,3-trioxo-1,
  2,3,4-tetrahydro-1l$^6$-benzo[1,2,3,4]thiadiazine-7-
  carboxylic acid 3-methoxy-benzylamide;

2-(4-Dimethylsulfamoyl-benzyl)-4-methyl-1,1,3-trioxo-
  1,2,3,4-tetrahydro-1l$^6$-benzo[1,2,4]thiadiazine-7-
  carboxylic acid benzylamide;

2-(4-Dimethylsulfamoyl-benzyl)-4-methyl-1,1,3-trioxo-
  1,2,3,4-tetrahydro-1l$^6$-benzo[1,2,4]thiadiazine-7-
  carboxylic acid (pyridin-4-ylmethyl)-amide;

2-(4-Dimethylsulfamoyl-benzyl)4-methyl-1,1,3-trioxo-1,
  2,3,4-tetrahydro-1l$^6$-benzo[1,2,3,4]thiadiazine-7-
  carboxylic acid (pyridin-3-ylmethyl)-amide;

2-(4-Dimethylsulfamoyl-benzyl)4-methyl-1,1,3-trioxo-1,
  2,3,4-tetrahydro-1l$^6$-benzo[1,2,4]thiadiazine-7-
  carboxylic acid 4-methoxy-benzylamide;

2-(4-Dimethylsulfamoyl-benzyl)-4-methyl-1,1,3-trioxo-
  1,2,3,4-tetrahydro-1l$^6$-benzo[1,2,4]thiadiazine-7-
  carboxylic acid 3-methoxy-benzylamide;

2-Benzyl-1,1,3-trioxo-1,2,3,4-tetrahydro-1l$^6$-benzo[1,2,
  3,4]thiadiazine-7-carboxylic acid benzylamide;

2-Benzyl-1,1,3-trioxo-1,2,3,4-tetrahydro-1l$^6$-benzo[1,2,
  3,4]thiadiazine-7-carboxylic acid (pyridin-4-
  ylmethyl)-amide;

2-Benzyl-1,1,3-trioxo-1,2,3,4-tetrahydro-1l$^6$-benzo[1,2,
  3,4]thiadiazine-7-carboxylic acid (pyridin-3-
  ylmethyl)-amide;

2-Benzyl-1,1,3-trioxo-1,2,3,4-tetrahydro-1l$^6$-benzo[1,2,
  3,4]thiadiazine-7-carboxylic acid 4-methoxy-
  benzylamide;

2-Benzyl-1,1,3-trioxo-1,2,3,4-tetrahydro-1l$^6$-benzo[1,2,
  3,4]thiadiazine-7-carboxylic acid 3-methoxy-
  benzylamide;

4-(7-Benzylcarbamoyl-1,1,3-trioxo-3,4-dihydro-1H-1l$^6$-
  benzo[1,2,4]thiadiazin-2-ylmethyl)-benzoic acid tert-
  butyl ester;

4-(1,1,3-Trioxo-7-[(pyridin-4-ylmethyl)-carbamoyl]-3,4-
  dihydro-1H-1l$^6$-benzo[1,2,4]thiadiazin-2-ylmethyl)-
  benzoic acid tert-butyl ester;

4-(1,1,3-Trioxo-7-[(pyridin-3-ylmethyl)-carbamoyl]-3,4-
  dihydro-1H-1l$^6$-benzo[1,2,4]thiadiazin-2-ylmethyl)-
  benzoic acid tert-butyl ester;

4-[7-(4-Methoxy-benzylcarbamoyl)-1,1,3-trioxo-3,4-
  dihydro-1H-1l$^6$ benzo[1,2,4]thiadiazin-2-ylmethyl)-
  benzoic acid tert-butyl ester;

4-[7-(3-Methoxy-benzylcarbamoyl)-1,1,3-trioxo-3,4-
  dihydro-1H-1l6-benzo[1,2,4]thiadiazin-2-ylmethyl)-
  benzoic acid tert-butyl ester;

4-(7-Benzylcarbamoyl-1,1,3-trioxo-3,4-dihydro-1H-1l$^6$-
  benzo[1,2,4]thiadiazin-2-ylmethyl)-benzoic acid;

4-(1,1,3-Trioxo-7-[(pyridin-4-ylmethyl)-carbamoyl]-3,4-
  dihydro-1H-1l$^6$-benzo[1,2,4]thiadiazin-2-ylmethyl)-
  benzoic acid;

4-(1,1,3-Trioxo-7-[(pyridin-3-ylmethyl)-carbamoyl]-3,4-
  dihydro-1H-1l$^6$-benzo[1,2,4]thiadiazin-2-ylmethyl)-
  benzoic acid;

4-[7-(4-Methoxy-benzylcarbamoyl)-1,1,3-trioxo-3,4-
  dihydro-1l$^6$-benzo[1,2,4]thiadiazin-2-ylmethyl)-
  benzoic acid;

4-[7-(3-Methoxy-benzylcarbamoyl)-1,1,3-trioxo-3,4-
  dihydro-1H-1l$^6$-benzo[1,2,4]thiadiazin-2-ylmethyl)-
  benzoic acid;

{4-(7-Benzylcarbamoyl-1,1,3-trioxo-3,4-dihydro-1H-1l$^6$
  benzo[1,2,4]thiadiazin-2-ylmethyl)-phenyl}-acetic
  acid tert-butyl ester;

{4-(1,1,3-Trioxo-7-[(pyridin-4-ylmethyl)-carbamoyl]-3,
  4-dihydro-1H-1l$^6$-benzo[1,2,4]thiadiazin-2-ylmethyl)-
  phenyl}-acetic acid tert-butyl ester;

{4-(1,1,3-Trioxo-7-[(pyridin-3-ylmethyl)-carbamoyl]-3,
  4-dihydro-1H-1l$^6$-benzo[1,2,4]thiadiazin-2-ylmethyl)-
  phenyl}-acetic acid tert-butyl ester;

{4-[7-(4-Methoxy-benzylcarbamoyl)-1,1,3-trioxo-3,4-
  dihydro-1H-1l$^6$-benzo[1,2,4]thiadiazin-2-ylmethyl)-
  phenyl}-acetic acid tert-butyl ester;

{4-[7-(3-Methoxy-benzylcarbamoyl)-1,1,3-trioxo-3,4-
  dihydro-1H-1l$^6$-benzo[1,2,4]thiadiazin-2-ylmethyl)-
  phenyl}-acetic acid tert-butyl ester;

{4-(7-Benzylcarbamoyl-1,1,3-trioxo-3,4-dihydro-1H-1l$^6$-
  benzo[1,2,4]thiadiazin-2-ylmethyl)-phenyl }-acetic
  acid;

{4-(1,1,3-Trioxo-7-[(pyridin-4-ylmethyl)-carbamoyl]-3,
  4-dihydro-1H-1l$^6$-benzo[1,2,4]thiadiazin-2-ylmethyl)-
  phenyl}-acetic acid;

{4-(1,1,3-Trioxo-7-[(pyridin-3-ylmethyl)-carbamoyl]-3,
  4-dihydro-1H-1l6-benzo[1,2,4]thiadiazin-2-
  ylmethyl)-phenyl}-acetic acid;

{4-[7-(4-Methoxy-benzylcarbamoyl) 1,1,3-trioxo-3,4-
  dihydro-1H-1l6-benzo[1,2,3,4]thiadiazin-2-ylmethyl)-
  phenyl }-acetic acid;

{4-[7-(3-Methoxy-benzylcarbamoyl)-1,1,3-trioxo-3,4-
  dihydro-1H-1l$^6$-benzo[1,2,4]thiadiazin-2-ylmethyl)-
  phenyl}-acetic acid;

2-(4-Methanesulfonyl-benzyl)-1,1,3-trioxo-1,2,3,4-
  tetrahydro-1l$^6$-benzo[1,2,4]thiadiazine-7-carboxylic
  acid benzylamide;

2-(4-Methanesulfonyl-benzyl)-1,1,3-trioxo-1,2,3,4-
  tetrahydro-1l$^6$-benzo[1,2,4]thiadiazine-7-carboxylic
  acid (pyridin-4-ylmethyl)-amide;

2-(4-Methanesulfonyl-benzyl)-1,1,3-trioxo-1,2,3,4-
  tetrahydro-1l$^6$-benzo[1,2,4]thiadiazine-7-carboxylic
  acid (pyridin-3-ylmethyl)-amide;

2-(4-Methanesulfonyl-benzyl)-1,1,3-trioxo-1,2,3,4-
  tetrahydro-1l$^6$-benzo[1,2,4]thiadiazine-7-carboxylic
  acid 4-methoxy-benzylamide;

2-(4-Methanesulfonyl-benzyl)-1,1,3-trioxo-1,2,3,4-
  tetrahydro-1l$^6$-benzo[1,2,4]thiadiazine-7-carboxylic
  acid 3-methoxy-benzylamide;

2-(4-Methylsulfamoyl-benzyl)-1,1,3-trioxo-1,2,3,4-
  tetrahydro-1l$^6$-benzo[1,2,3,4]thiadiazine-7-carboxylic
  acid benzylamide;

2-(4-Methylsulfamoyl-benzyl)-1,1,3-trioxo-1,2,3,4-
  tetrahydro-1l$^6$-benzo[1,2,4]thiadiazine-7-carboxylic
  acid (pyridin-4-ylmethyl)-amide;

2-(4-Methylsulfamoyl-benzyl)-1,1,3-trioxo-1,2,3,4-
  tetrahydro-1l$^6$-benzo[1,2,3,4]thiadiazine-7-carboxylic
  acid (pyridin-3-ylmethyl)-amide;

2-(4-Methylsulfamoyl-benzyl)-1,1,3-trioxo-1,2,3,4-
  tetrahydro-1l$^6$-benzo[1,2,3,4]thiadiazine-7-carboxylic
  acid 4-methoxy-benzylamide;

2-(4-Methylsulfamoyl-benzyl)-1,1,3-trioxo-1,2,3,4-tetrahydro-1l$^6$-benzo[1,2,4]thiadiazine-7-carboxylic acid 3-methoxy-benzylamide;

2-(4-Dimethylsulfamoyl-benzyl)-1,1,3-trioxo-1,2,3,4-tetrahydro-1l$^6$-benzo[1,2,4]thiadiazine-7-carboxylic acid benzylamide;

2-(4-Dimethylsulfamoyl-benzyl)-1,1,3-trioxo-1,2,3,4-tetrahydro-1l$^6$-benzo[1,2,4]thiadiazine-7-carboxylic acid (pyridin-4-ylmethyl)-amide;

2-(4-Dimethylsulfamoyl-benzyl)-1,1,3-trioxo-1,2,3,4-tetrahydro-1l$^6$-benzo[1,2,4]thiadiazine-7-carboxylic acid (pyridin-3-ylmethyl)-amide;

2-(4-Dimethylsulfamoyl-benzyl)-1,1,3-trioxo-1,2,3,4-tetrahydro-1l$^6$-benzo[1,2,4]thiadiazine-7-carboxylic acid 4-methoxy-benzylamide; and 2-(4-Dimethylsulfamoyl-benzyl)-1,1,3-trioxo-1,2,3,4-tetrahydro-1l$^6$-benzo[1,2,4]thiadiazine-7-carboxylic acid 3-methoxy-benzylamide.

A further embodiment of this invention is use of a compound of Formula I, or a pharmaceutically acceptable salt thereof, in the manufacture of a medicament for the treatment of a disease mediated by an MMP-13 enzyme.

Another invention embodiment is use of a compound of Formula II, or a pharmaceutically acceptable salt thereof, in the manufacture of a medicament for the treatment of a disease mediated by an MMP-13 enzyme.

Another invention embodiment is use of a compound of Formula I, or a pharmaceutically acceptable salt thereof, in the manufacture of a medicament for the treatment of cancer.

Another invention embodiment is use of a compound of Formula I, or a pharmaceutically acceptable salt thereof, in the manufacture of a medicament for the treatment of rheumatoid arthritis.

Another invention embodiment is use of a compound of Formula I, or a pharmaceutically acceptable salt thereof, in the manufacture of a medicament for the treatment of osteoarthritis.

Another invention embodiment is use of a compound of Formula I, or a pharmaceutically acceptable salt thereof, in the manufacture of a medicament for the treatment of heart failure.

A further embodiment of this invention is a pharmaceutical composition, comprising a compound of Formula I, or a pharmaceutically acceptable salt thereof, admixed with a pharmaceutically acceptable carrier, excipient, or diluent.

Another invention embodiment is a pharmaceutical composition, comprising a compound of Formula II, or a pharmaceutically acceptable salt thereof, together with a pharmaceutically acceptable carrier, excipient, or diluent.

Another embodiment of this invention is a method for inhibiting an MMP-13 enzyme in an animal, comprising administering to the animal an MMP-13 inhibiting amount of a compound of Formula I, or a pharmaceutically acceptable salt thereof.

A further embodiment is a method for treating a disease mediated by an MMP-13 enzyme, comprising administering to a patient suffering from such a disease an effective amount of a compound of Formula I, or a pharmaceutically acceptable salt thereof.

Another invention embodiment is a method for treating a cancer, comprising administering to a patient suffering from such a disease an anticancer effective amount of a compound of Formula I, or a pharmaceutically acceptable salt thereof.

Another invention embodiment is a method for treating breast carcinoma, comprising administering to a patient suffering from such a disease an anticancer effective amount of a compound of Formula I, or a pharmaceutically acceptable salt thereof.

Another invention embodiment is a method for treating a rheumatoid arthritis, comprising administering to a patient suffering from such a disease an effective amount of a compound of Formula I, or a pharmaceutically acceptable salt thereof.

Another invention embodiment is a method for treating a osteoarthritis, comprising administering to a patient suffering from such a disease an effective amount of a compound of Formula I, or a pharmaceutically acceptable salt thereof.

Another invention embodiment is a method for treating a heart failure, comprising administering to a patient suffering from such a disease an effective amount of a compound of Formula I, or a pharmaceutically acceptable salt thereof.

Another invention embodiment is a method for treating a inflammation, comprising administering to a patient suffering from such a disease an effective amount of a compound of Formula I, or a pharmaceutically acceptable salt thereof.

Another embodiment of the present invention is a process for preparing a compound of Formula I

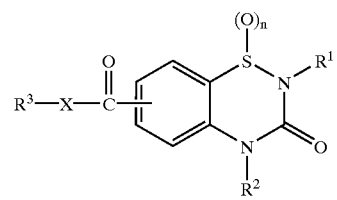

or a pharmaceutically acceptable salt thereof, wherein:

n is 0, 1, or 2;

X is O or NH;

$R^2$ is H, $C_1$–$C_6$ alkyl, or $C_1$–$C_6$ substituted alkyl;

$R^1$ and $R^3$ independently are H, acyl, substituted acyl, $C_1$–$C_6$ alkyl, $C_1$–$C_6$ substituted alkyl, $C_2$–$C_6$ alkenyl, $C_2$–$C_6$ substituted alkenyl, $C_2$–$C_6$ alkynyl, $C_1$–$C_6$ alkynyl, $(CH_2)_m$ aryl, $(CH_2)_m$ substituted aryl, $(CH_2)_m$ heteroaryl, $(CH_2)_m$ substituted heteroaryl, $(CH_2)_m$ cycloalkyl, or $(CH_2)_m$ substituted cycloalkyl; and each m independently is an integer of from 0 to 6, with the proviso that $R_3$ is not $(CH_2)_m$ biphenyl or $(CH_2)_m$ substituted biphenyl, the process comprising the step of:

contacting a compound of Formula (A)

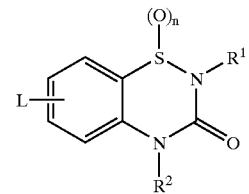

wherein n, $R^1$, and $R^2$ are as defined above, and

L is $CO_2H$, $CO_2M$, C(=O)-halo, C(=O)—$OR^7$, C(=O)$NR^8R^9$, C(=O)—C(halo)$_3$, or C≡N, wherein $R^7$ is pentafluorophenyl, C(=O)$R^2$, or S(O)$R^2$, wherein $R^2$ is as defined above;

$R^8$ and $R^9$ are taken together with the nitrogen atom to which they are attached to form imidazol-1-yl, phthalimid-1-yl, benzotriazol-1-yl, or tetrazol-1-yl; and M is an alkali earth metal cation or alkaline earth metal cation, with a solvent and a compound of Formula (B)

$$D-R^3 \quad (B)$$

wherein R3 is as defined above and D is HO, H2N, MO, or MN(H), wherein M is as defined above, optionally in the presence of from 1 to 3 agents selected from:

a coupling agent, a tertiary organic amine, an acid catalyst, a base catalyst, an acid halide, and an acid anhydride.

Another invention embodiment is the invention process wherein n is 2.

Another invention embodiment is the invention process, wherein n is 2 and X is O.

Another invention embodiment is the invention process, wherein n is 2 and X is NH.

Another invention embodiment is the invention process, wherein R1 and R3 independently are $(CH_2)_m$ aryl, $(CH_2)_m$ substituted aryl, $(CH_2)_m$ heteroaryl, $(CH_2)_m$ substituted heteroaryl.

Another invention embodiment is any one of the above embodiments of the invention process wherein L is $CO_2H$, $CO_2M$, or C(=O)-halo.

DETAILED DESCRIPTION OF THE INVENTION

The compounds provided by this invention are those defined by Formula I. In Formula I, $R^1$ to $R^3$ include "$C_1$–$C_6$ alkyl" groups. These are straight and branched carbon chains having from 1 to 6 carbon atoms. Examples of such alkyl groups include methyl, ethyl, isopropyl, tert-butyl, neopentyl, and n-hexyl. The alkyl groups can be substituted if desired, for instance with groups such as hydroxy, alkoxy, amino, alkyl and dialkylamino, alkanoyl, acyl, halo, trifluoromethyl, carboxy, nitro, and cyano.

"Alkenyl" means straight and branched hydrocarbon radicals having from 2 to 6 carbon atoms and one double bond and includes ethenyl, 3-buten-1-yl, 2-ethenylbutyl, 3-hexen-1-yl, and the like.

"Alkynyl" means straight and branched hydrocarbon radicals having from 2 to 6 carbon atoms and one triple bond and includes ethynyl, 3-butyn-1-yl, propynyl, 2-butyn-1-yl, 3-pentyn-1-yl, and the like.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocycle" or "heterocyclyl", which means a cycloalkyl group also bearing at least one heteroatom selected from O, S, or $NR^2$, examples being oxiranyl, pyrrolidinyl, piperidyl, tetrahydropyran, and morpholine.

"Alkoxy" refers to the alkyl groups mentioned above bound through oxygen, examples of which include methoxy, ethoxy, isopropoxy, tert-butoxy, and the like. In addition, alkoxy refers to polyethers such as —O—$(CH_2)_2$—O—$CH_3$, and the like. "Thioalkoxy" is an alkoxy group wherein the O is replaced by an S.

"Alkanoyl" groups are alkyl linked through a carbonyl, ie, $C_1$—$C_5$—C(O)—. Such groups include formyl, acetyl, propionyl, butyryl, and isobutyryl.

"Acyl" means an R group that is a $C_1$–$C_6$ alkyl or aryl (Ar) group bonded through a carbonyl group, i.e., R—C(O)—, wherein $C_1$–$C_6$ alkyl and aryl are as defined above and below, respectively. The phrase "substituted acyl" means an R group that is a substituted $C_1$–$C_6$ alkyl or a substituted aryl (substituted Ar) group bonded through a carbonyl group. For example, substituted acyl includes substituted alkanoyl, wherein the alkyl portion can be substituted by $NR^4R^5$ or a carboxylic or heterocyclic group. Typical acyl groups include acetyl, benzoyl, and the like. Typical substituted acyl groups include trifluoroacetyl, 4-carboxybenzoyl, and the like.

The alkyl, alkenyl, alkoxy, and alkynyl groups described above are optionally substituted, preferably by 1 to 3 groups selected from $NR^4R^5$, phenyl, substituted phenyl, $(CH_2)_m$—C(O) phenyl, $(CH_2)_m$ C(O) substituted phenyl, $(CH_2)_m$—S(O)$_{0-2}$ phenyl, $(CH_2)_m$ S(O)$_{0-2}$ substituted phenyl, $(CH_2)_m$—C(O) heteroaryl, $(CH_2)_m$ C(O) substituted heteroaryl, $(CH_2)_m$—S(O)$_{0-2}$ heteroaryl, $(CH_2)_m$—S(O)$_{0-2}$ substituted heteroaryl, $(CH_2)_m$ cycloalkyl, heterocycle, thio $C_1$–$C_6$ alkyl, $C_1$–$C_6$ alkoxy, hydroxy, acyl, carboxy, alkanoyl, $C_1$–$C_6$ alkoxycarbonyl, halo, nitro, nitrile, cycloalkyl, and a 5-or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$–$C_6$ alkyl or $(CH_2)_y$Ph where y is 1, 2, or 3. Perhalo and polyhalo substitution is also embraced.

$R^4$ and $R^5$ independently are hydrogen, $C_1$–$C_6$ alkyl, $C_2$–$C_6$ alkenyl, $C_2$–$C_6$ alkynyl, acyl, $(CH_2)_m$ aryl, $(CH_2)_m$ heteroaryl, $(CH_2)_m$ cycloalkyl, wherein these groups may be unsubstituted or substituted as described herein, or $R^4$ and $R^5$ are taken together with the nitrogen atom to which they are attached to form a 3- to 7-membered ring containing carbon atoms, the nitrogen atom bearing $R^4$ and $R^5$, and optionally 1 or 2 heteroatoms selected from O, S, NH, and $NR^2$, wherein $R^2$ is as defined above, the ring optionally may be substituted with oxo ("=O") on a carbon atom.

Examples of $NR^4R^5$ groups include amino, methylamino, di-isopropylamino, acetyl amino, propionyl amino, 3-aminopropyl amino, 3-ethylaminobutyl amino, 3-di-n-propylamino-propyl amino, 4-diethylaminobutyl amino, and 3-carboxypropionyl amino. $R^4$ and $R^5$ can be taken together with the nitrogen to which they are attached to form a ring having 3 to 7 carbon atoms and 1, 2, or 3 heteroatoms selected from the group consisting of nitrogen, substituted nitrogen, oxygen, and sulfur. Examples of such cyclic $NR^4R^5$ groups include pyrrolidinyl, piperazinyl, 4-methylpiperazinyl, 4-benzylpiperazinyl, pyridinyl, piperidinyl, pyrazinyl, morpholinyl, and the like.

"Halo" includes fluoro, chloro, bromo, and iodo.

Examples of substituted alkyl groups include 2-aminoethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, benzyl(Bn), 3-morpholinopropyl, piperazinylmethyl, pyridyl-4-methyl(Py-4-me), 3-(pyridyl-4-thio)propyl, and 2-(4-methylpiperazinyl)ethyl.

Examples of substituted alkynyl groups include 2-methoxyethynyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxhexyloxy, and the like.

Further, examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrinidylbutyl, 3-imidazolidin-1-ylpropyl, 4-tetrahydrothiazol-3-yl-butyl, phenylmethyl, 3-chlorophenylmethyl, and the like.

The terms "Ar" and "aryl" refer to unsubstituted and substituted aromatic groups. Heteroaryl groups have from 4 to 10 ring atoms, from 1 to 4 of which are independently selected from the group consisting of O, S, and N. Preferred heteroaryl groups have 1 or 2 heteroatoms in a 5- or 6-membered aromatic ring. Mono- and bicyclic aromatic ring systems are included in the definition of aryl and heteroaryl. Typical aryl and heteroaryl groups include phenyl, 3-chlorophenyl, 3,4-methylenedioxyphenyl, 2,6-dibromophenyl, pyridyl, 3-methylpyridyl, 4-thiopyridyl, benzothienyl, 2,4,6-tribromophenyl, 4-ethylbenzothienyl, furanyl, 3,4-diethylfuranyl, naphthyl, 4,7-dichloronaphthyl, morpholinyl, indolyl, benzotriazolyl, indazolyl, pyrrole, pyrazole, imidazole, thiazole, and the like.

Preferred Ar groups are phenyl or naphthyl, and phenyl or naphthyl substituted by 1, 2, or 3 groups independently selected from the group consisting of alkyl, alkoxy, thio, thioalkyl, thioalkoxy, $(CH_2)_mN(R^4)S(O)_2(C_1-C_6$ alkyl), $(CH_2)_mS(O)_2NR^4R^5$, wherein $R^4$, $R^5$, and m are as defined above, $S(O)_2NR^4R^5$, $C(O)NR^4R^5$, $N(H)C(O)NR^4R^5$, O—C$(O)NR^4R^5$, halo, hydroxy, —COOR$^6$, trifluoromethyl, nitro, amino of the formula —NR$^4$R$^5$, C(O)NR$^4$R$^5$, S(O)C$_1$–C$_6$ alkyl, S(O)$_2$C$_1$–C$_6$ alkyl, 5-membered heteroaryl, N(R$^5$)C(O)O(C$_1$–C$_6$ alkyl), and T(CH$_2$)$_p$QR$^4$ or T(CH$_2$)$_p$CO$_2$R$^4$, wherein p is 1 to 6, T is O, S, SO, SO$_2$, NR$^4$, N(O)R$^4$, NR$^4$R$^6$Y, or CR$^4$R$^5$, Q is O, S, SO, SO$_2$, NR$^4$, N(O)R$^5$, or NR$^5$R$^6$Y, wherein R$^4$ and R$^5$ are as described above, Y is a counter ion such as halo, R$^6$ is H, C$_1$–C$_6$ alkyl, or substituted C$_1$–C$_6$ alkyl, for example, methyl, trichloroethyl, diphenylmethyl, and the like. The alkyl and alkoxy groups can be substituted as defined above. For example, typical groups are carboxyalkyl, alkoxycarbonylalkyl, hydroxyalkyl, hydroxyalkoxy, and alkoxyalkyl. Examples of substituted phenyl are 3-methoxyphenyl, 2,6-dichlorophenyl, 3-nitrophenyl, 4-dimethylaminophenyl, and biphenyl. Examples of quaternary ammonium groups defined by NR$^4$R$^6$Y are trimethylammonium chloride and triethylammonium bromide.

Heteroaryl groups may be substituted with up to 3 groups independently selected from the 1, 2, or 3 groups described above for substituted phenyl.

The phrase "tertiary organic amine" means a trisubstituted nitrogen group wherein the 3 substituents are independently selected from C$_1$–C$_{12}$ alkyl, C$_3$–C$_{12}$ cycloalkyl, benzyl, or wherein two of the substituents are taken together with the nitrogen atom to which they are attached to form a 5- or 6-membered, monocyclic heterocycle containing one nitrogen atom and carbon atoms, and the third substituent is selected from C$_1$–C$_{12}$ alkyl and benzyl, or wherein the three substituents are taken together with the nitrogen atom to which they are attached to form a 7- to 12-membered bicyclic heterocycle containing 1 or 2 nitrogen atoms and carbon atoms, and optionally a C=N double bond when 2 nitrogen atoms are present. Illustrative examples of tertiary organic amine include triethylamine, diisopropylethylamine, benzyl diethylamino, dicyclohexylmethyl-amine, 1,8-diazabicycle[5.4.0]undec-7-ene ("DBU"), 1,4-diazabicyclo[2.2.2]octane ("TED"), and 1,5-diazabicycle[4.3.0]non-5-ene.

The term "coupling agent" includes any reagent, or any combination of two, three, or four reagents, conventionally used to promote coupling of a carboxylic acid, or a pharmaceutically acceptable salt thereof, with an alcohol or an amine to yield a carboxylic ester or carboxylic amide, respectively. The coupling agents are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5$^{th}$ edition, by Jerry March, Wiley-Interscience, New York (2001). Illustrative examples of coupling agents include N,N'-carbonyldiimidazole ("CDI"), N,N'-dicyclohexylcarbodiimide ("DCC"), triphenylphosphine with diethylazodicarboxylate, bis(2-oxo-3-oxazolidinyl) phosphinic chloride ("BOP-Cl"), POCl$_3$, Ti(Cl)$_4$, and 1-(3-dimethylaminopropyl)-3-ethylcarbodiimide hydrochloride ("EDAC").

The phrase "acid catalyst" means any protic or Lewis acid that is conventionally used to catalyze coupling of a carboxylic acid, or a pharmaceutically acceptable salt thereof, a nitrile, carboxylic ester, carboxylic amide, carboxylic acid halide, or carboxylic acid anhydride with an alcohol or an amine to yield a carboxylic ester or carboxylic amide, respectively. The acid catalysts are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5$^{th}$ edition, by Jerry March, Wiley-Interscience, New York (2001). Illustrative examples include anhydrous hydrogen chloride, hydrochloric acid, hydrogen bromide in acetic acid, zinc chloride, titanium tetrachloride, acetic acid, trifluoroacetic acid, phenol, sulfuric acid, methanesulfonic acid, magnesium sulfate, Amberlyst-15 resin, silica gel, and the like.

It should be appreciated that a nitrile may be contacted with an alcohol or an amine in the presence of an acid catalyst, and the resulting intermediate imidate or amidine, respectively, may be contacted with water to yield the carboxylic ester or carboxylic amide, respectively.

The phrase "base catalyst" means any base that is conventionally used to catalyze coupling of a carboxylic acid, or a pharmaceutically acceptable salt thereof, carboxylic ester, carboxylic amide, carboxylic acid halide, or carboxylic acid anhydride with an alcohol or an amine to yield a carboxylic ester or carboxylic amide, respectively. The base catalysts are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5$^{th}$ edition, by Jerry March, Wiley-Interscience, New York (2001). Illustrative examples include sodium hydroxide, sodium hydride, potassium tert-butoxide, a tertiary organic amine, titanium tetraisopropoxide, sodium methoxide, sodium acetate, sodium bicarbonate, potassium carbonate, basic alumina, and the like.

The phrase "acid halide" means any carboxylic acid halide or sulfonic acid halide that is conventionally used to catalyze coupling of a carboxylic acid, or a pharmaceutically acceptable salt thereof, with an alcohol or an amine to yield a carboxylic ester or carboxylic amide, respectively. The acid halides are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series Compendium of *Organic Synthetic Methods* (1989) by Wiley-Interscience; and the text *Advanced Organic Chemistry*, 5$^{th}$ edition, by Jerry March, Wiley-Interscience, New York (2001). Illustrative examples include acetyl chloride, trifluoromethanesulfonyl chloride, 2,2-dimethylacetyl bromide, para-toluenesulfonyl chloride, pentafluoro-benzoyl chloride, and the like.

The phrase "acid anhydride" means any carboxylic acid anhydride or sulfonic acid anhydride that is conventionally used to catalyze coupling of a carboxylic acid, or a pharmaceutically acceptable salt thereof, with an alcohol or an amine to yield a carboxylic ester or carboxylic amide, respectively. The acid anhydrides are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5$^{th}$ edition, by Jerry March, Wiley-Interscience, New York (2001). Illustrative examples include acetic anhydride, trifluoroacetic anhydride, trifluoromethanesulfonic acid anhydride, pentafluoro-benzoic anhydride, mixed anhydrides like trifluoroacetyloxycarbonylmethyl, and the like.

The term "halide" includes fluoride, chloride, bromide, and iodide.

The phrase "coupling catalyst" means any metal catalyst, preferably a transition metal catalyst, that is conventionally used to catalyze coupling of an aryl halide, aryl trifluoromethanesulfonate, heteroaryl halide, or heteroaryl trifluoromethanesulfonate, or activated derivatives thereof, including arylboronic acids, heteroarylboronic acids, aryl stannanes, heteroarylstannanes, aryl magnesium halides, heteroaryl magnesium halides, aryl lithiums, or heteroaryl lithiums, with an terminal alkyne to yield an arylalkyne or heteroarylalkyne. The coupling catalysts are described in *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; and the text *Advanced Organic Chemistry*, 5$^{th}$ edition, by Jerry March, Wiley-Interscience, New York (2001). Illustrative examples of coupling catalysts include tetrakis (triphenylphosphine)palladium (0), palladium (II) chloride, palladium (II) acetate, iron (III) chloride, Heck reaction catalysts, Suzuki reaction catalysts, Stille reaction catalysts, and the like.

The group "$S(O)_{0-2}$" means S, S(=O), or $S(=O)_2$.

The descriptors "$1l^6$" and "$1\lambda^6$" are synonymous.

The term "patient" means a mammal. Preferred patients include humans, cats, dogs, cows, horses, pigs, and sheep.

The term "animal" means a mammal. Preferred animals are include humans, rats, mice, guinea pigs, rabbits, monkeys, cats, dogs, cows, horses, pigs, and sheep.

The phrases "therapeutically effective amount" and "effective amount" are synonymous unless otherwise indicated, and mean an amount of a compound of the present invention that is sufficient to improve the condition, disease, or disorder being treated. Determination of a therapeutically effective amount, as well as other factors related to effective administration of a compound of the present invention to a patient in need of treatment, including dosage forms, routes of administration, and frequency of dosing, may depend upon the particulars of the condition that is encountered, including the patient and condition being treated, the severity of the condition in a particular patient, the particular compound being employed, the particular route of administration being employed, the frequency of dosing, and the particular formulation being employed. Determination of a therapeutically effective treatment regimen for a patient is within the level of ordinary skill in the medical or veterinarian arts. In clinical use, an effective amount may be the amount that is recommended by the U.S. Food and Drug Administration, or an equivalent foreign agency.

The phrase "admixed" or "in admixture" means the ingredients so mixed comprise either a heterogeneous or homogeneous mixture. Preferred is a homogeneous mixture.

The phrases "pharmaceutical preparation" and "preparation" are synonymous unless otherwise indicated, and include the formulation of the active compound with encapsulating material as a carrier providing a capsule in which the active component, with or without other carriers, is surrounded by a carrier, which is thus in association with it. Similarly, cachets and lozenges are included. Pharmaceutical preparations are fully described below.

The phrase "anticancer effective amount" means an amount of invention compound, or a pharmaceutically acceptable salt thereof, sufficient to inhibit, halt, or cause regression of the cancer being treated in a particular patient or patient population. For example in humans or other mammals, an anticancer effective amount can be determined experimentally in a laboratory or clinical setting, or may be the amount required by the guidelines of the United States Food and Drug Administration, or equivalent foreign agency, for the particular cancer and patient being treated.

The phrase "MMP-13 inhibiting amount" means an amount of invention compound, or a pharmaceutically acceptable salt thereof, sufficient to inhibit an enzyme matrix metalloproteinase-13, including a truncated form thereof, including a catalytic domain thereof, in a particular animal or animal population. For example in a human or other mammal, an MMP-13 inhibiting amount can be determined experimentally in a laboratory or clinical setting, or may be the amount required by the guidelines of the United States Food and Drug Administration, or equivalent foreign agency, for the particular MMP-13 enzyme and patient being treated.

It should be appreciated that the matrix metalloproteinases include the following enzymes:

MMP-1, also known as interstitial collagenase, collagenase-1, or fibroblast-type collagenase;

MMP-2, also known as gelatinase A or 72 kDa Type IV collagenase;

MMP-3, also known as stromelysin or stromelysin-1;

MMP-7, also known as matrilysin or PUMP-1;

MMP-8, also known as collagenase-2, neutrophil collagenase, or polymorphonuclear-type ("PMN-type") collagenase;

MMP-9, also known as gelatinase B or 92 kDa Type IV collagenase;

MMP-10, also known as stromelysin-2;

MMP-11, also known as stromelysin-3;

MMP-12, also known as metalloelastase;

MMP-13, also known as collagenase-3;

MMP-14, also known as membrane-type ("MT") 1-MMP or MT1-MMP;

MMP-15, also known as MT2-MMP;

MMP-16, also known as MT3-MMP;
MMP-17, also known as MT4-MMP;
MMP-18; and
MMP-19.

Other MMPs are known, including MMP-26, which is also known as matrilysin-2.

One aspect of the present invention is a compound of Formula I, or a pharmaceutically acceptable salt thereof, that is a selective inhibitor of the enzyme MMP-13. A selective inhibitor of MMP-13, as used in the present invention, is a compound that is ≧5 times more potent in vitro versus MMP-13 than versus at least one other matrix metalloproteinase enzyme such as, for example, MMP-1, MMP-2, MMP-3, MMP-7, MMP-8, MMP-9, or MMP-14, or versus tumor necrosis factor alpha convertase ("TACE"). A preferred aspect of the present invention is a compound that is a selective inhibitor of MMP-13 versus MMP-1.

Another aspect of the present invention is a compound of Formula I, or a pharmaceutically acceptable salt thereof, that is a selective inhibitor of MMP-13 versus 2, 3, 4, 5, 6, or 7 other MMP enzymes, or versus TACE and 1, 2, 3, 4, 5, 6, or 7 other MMP enzymes. O Another aspect of the present invention is a compound of Formula I, or a pharmaceutically acceptable salt thereof, that is ≧10 times, ≧20 times, ≧50 times, ≧100 times, or ≧1000 times more potent versus MMP-13 than versus at least one of any other MMP enzyme or TACE.

It should be appreciated that determination of proper dosage forms, dosage amounts, and routes of administration, is within the level of ordinary skill in the pharmaceutical and medical arts, and is described below.

The term "IC$_{50}$" means the concentration of test compound required to inhibit activity of a biological target, such as a receptor or enzyme, by 50%.

The phrase "catalytic domain" means the domain containing a catalytic zinc cation of the MMP enzyme, wherein the MMP enzyme contains 2 or more domains. A catalytic domain includes truncated forms thereof that retain at least some of the catalytic activity of MMP-13 or MMP-13CD. For example, the collagenases, of which MMP-13 is a member, have been reported to contain a signal peptide domain, a propeptide domain, a catalytic domain, and a hemopexin-like domain (Ye Qi-Zhuang, Hupe D., Johnson L., Current Medicinal Chemistry, 1996;3:407–418).

The phrase "a method for inhibiting MMP-13" includes methods of inhibiting full length MMP-13, truncated forms thereof that retain catalytic activity, including forms that contain the catalytic domain of MMP-13, as well as the catalytic domain of MMP-13 alone, and truncated forms of the catalytic domain of MMP-13 that retain at least some catalytic activity.

It should be appreciated that it has been shown previously (Ye Qi-Zhuang, et al., 1996, supra) that inhibitor activity against a catalytic domain of an MMP is predictive of the inhibitor activity against the respective full-length enzyme.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention. Some of the invention compounds may have one or more chiral centers, and as such can exist as individual enantiomers and mixtures. This invention contemplates all racemic mixtures, pure enantiomers, as well as geometric and positional isomers.

The compounds of Formulas I and II are capable of further forming both pharmaceutically acceptable salts, including but not limited to acid addition and/or base salts, solvates, and N-oxides of a compound of Formulas I and II. This invention also provides pharmaceutical formulations comprising a compound of Formulas I and II together with a pharmaceutically acceptable carrier, diluent, or excipient therefor. All of these forms can be used in the method of the present invention.

Pharmaceutically acceptable acid addition salts of the compounds of Formulas I and II include salts derived form inorganic acids such as hydrochloric, nitric, phosphoric, sulfuric, hydrobromic, hydroiodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," J. of *Pharmaceutical Science,* 1977;66:1–19.

The acid addition salts of the basic compounds are prepared by contacting the free-base form with a sufficient amount of the desired acid to produce the salt in the conventional manner. The free-base form may be regenerated by contacting the salt form with a base and isolating the free base in the conventional manner. The free-base forms differ from their respective salt forms somewhat in certain physical properties such as solubility in polar solvents, but otherwise the salts are equivalent to their respective free base for purposes of the present invention.

Pharmaceutically acceptable base addition salts (for example when carboxylic acid groups are present) are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

The compounds of the present invention can be formulated and administered in a wide variety of oral and parenteral dosage forms, including parenteral, oral, transdermal, and rectal administration. All that is required is that an MMP inhibitor be administered to a mammal suffering from a disease in an effective amount, which is that amount required to cause an improvement in the disease and/or the symptoms associated with such disease. It will be recognized by those skilled in the art that the dosage forms provided herein may comprise as the active component, a compound of Formula I or a corresponding pharmaceutically acceptable salt or solvate of a compound of Formula I, admixed with any conventional excipient, diluent, or carrier.

A compound of Formula I, or a pharmaceutically acceptable salt thereof, may be prepared by one of ordinary skill in the art of organic chemistry by procedures found in the chemical literature such as, for example, Reagents for Organic Synthesis, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; the text *Advanced Organic Chemistry*, 5th edition, by Jerry March, Wiley-Interscience, New York (2001); or the *Handbook of Heterocyclic Chemistry*, by Alan R. Katritzky, Pergamon Press Ltd., London, (1985), to name a few. Alternatively, a skilled artisan may find methods useful for preparing the invention compounds in the chemical literature by searching widely available databases such as, for example, those available from the *Chemical Abstracts Service*, Columbus, Ohio, or MDL Information Systems GmbH (formerly *Beilstein Information Systems GmbH*), Frankfurt, Germany.

Preparations of the compounds of the present invention may use starting materials, reagents, solvents, and catalysts that may be purchased from commercial sources or they may be readily prepared by adapting procedures in the references or resources cited above. Commercial sources of starting materials, reagents, solvents, and catalysts useful in preparing invention compounds include, for example, The Aldrich Chemical Company, and other subsidiaries of Sigma-Aldrich Corporation, St. Louis, Mo., BACHEM, BACHEM A.G., Switzerland, or Lancaster Synthesis Ltd., United Kingdom.

Reagents for *Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; the text *Advanced Organic Chemistry*, 5th edition, by Jerry March, Wiley-Interscience, New York (2001); and the *Handbook of Heterocyclic Chemistry*, by Alan R. Katritzky, Pergamon Press Ltd., London, (1985) are hereby incorporated by reference.

The invention compounds are prepared by methods well-known to those skilled in the art of organic chemistry. The compounds of Formula I are prepared utilizing commercially available starting materials, or reactants that are readily prepared by standard organic synthetic techniques. A typical synthesis of the invention compounds of Formula I is shown in Scheme 1 below. The first step in Scheme 1 comprises reacting a substituted ($R^2$) anthranilate of formula (A) with N-chlorosulfonyl isocyanate (CSI) followed by an appropriate Lewis acid such as aluminum trichloride in the manner described by Girared Y et al., (*J. Chem. Soc. Perkins I*, 1979:1043–1047). The resulting 1,2,4-benzothiadiazone carboxylate (B) can then be alkylated in the 3 position to give the compound (C) (for example by reaction with a common alkylating agent such as an alkyl halide, generally in the presence of a base such as triethylamine or pyridine). Simple hydrolysis of the ester under standard conditions (eg, alkaline conditions) affords the carboxylic acid (D). This acid can then be further reacted with alcohols or amines to provide the desired ester or carboxylic amide (E) using standard coupling conditions known to those skilled in the art (such as 1,3-dicyclohexylcarbodiimide (DCC) activation, in situ acid halide formation, 1,1-carbonyldiimidazole (CDI) activation, etc.). The invention compounds can be isolated and purified by standard methods such as crystallization (from solvents such as alcohols, alkyl esters, haloalkanes, alkanes) and chromatography over solid supports such as silica gel (eluting with solvents such as dichloromethane, ethyl acetate, methanol). Optically active compounds can be isolated by standard methods, for example fractional crystallization, chiral synthesis, and classical resolution.

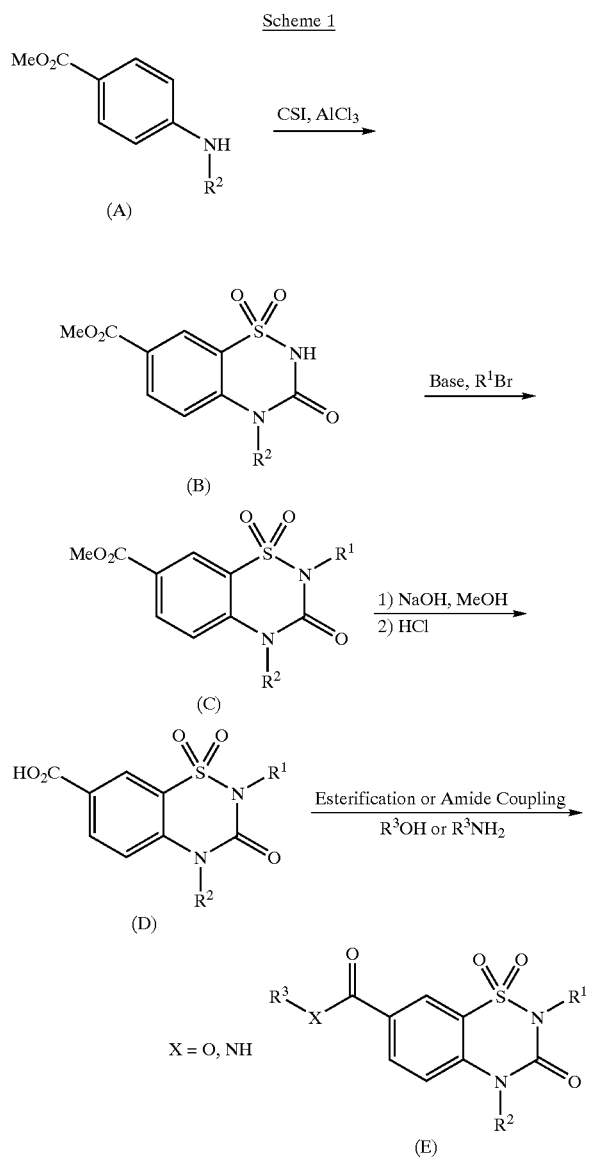

An alternative synthesis of the benzothiadiazines of the invention is given in Scheme 2. In this case, a substituted ($R^2$) anthranilate of formula (A) is reacted with excess chlorosulfonic acid to give the sulfonyl chloride (F). This sulfonyl chloride is readily converted to the corresponding sulfonamide (G) by reaction with saturated ammonium hydroxide or liquid ammonia. Reaction of this sulfonamide with urea (or a similar C=O synthon such as phosgene or triphosgene) affords the desired 1,1,3-trioxo-1,2,3,4-tetrahydro-11$^6$-benzo[1,2,4]thiadiazine ring system (B) which can be further elaborated to the compounds of the present invention as demonstrated in Scheme 1.

Scheme 2

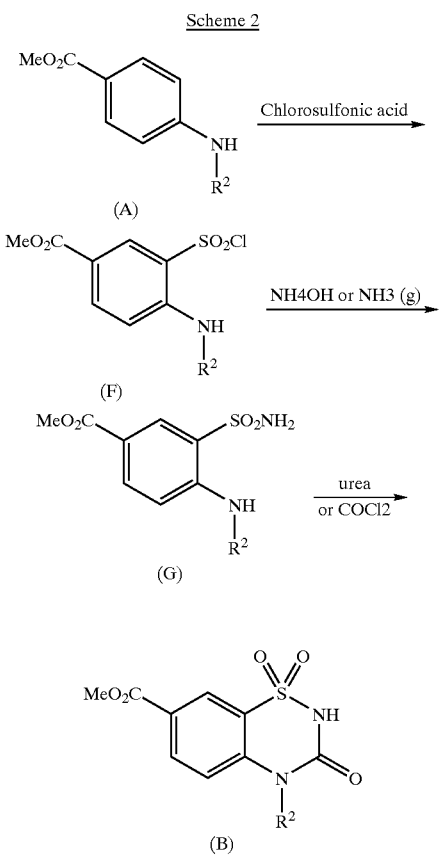

During the synthesis of some of the invention compounds, it may be desirable to protect reactive functional groups such as hydroxy, amino, and carboxylic groups, so as to avoid unwanted side reactions. The use of protecting groups in synthetic organic chemistry is well established and is fully described by Greene and Wuts in "Protecting Groups in Organic Synthesis" (John Wiley & Son Press, 3$^{rd}$ ed). Examples of common amino protecting groups include acyl groups such as formyl and acetyl, and arylalkyl groups such as benzyl. Typical hydroxy protecting groups include ether forming groups such as methyl and ethyl, and acyl groups such as acetyl and tert-butoxycarbonyl (tBOC). Carboxylic acids generally are protected as esters, for example 2,2,2-trichloroethyl and benzyl. These protecting groups are readily cleaved by standard methods when desired.

Sulfoxides and sulfones of Formula 1, wherein n is 1 or 2, are prepared by oxidation of the corresponding sulfides with one or two equivalents of an oxidizing agent such as peracetic acid or meta-chloroperbenzoic acid.

The following detailed examples further illustrate the synthesis of typical invention compounds of Formula I. In the examples where the compound of the example is characterized by elemental analysis of, for illustration, carbon, hydrogen, and nitrogen, the term "C,H,N" means the percents found of carbon, hydrogen, and nitrogen were within ±0.4% of their respective theoretical values for the molecular formula recited. The examples are representative only and are not to be construed as limiting the invention in any respect.

All references cited herein are incorporated by reference.

EXAMPLE 1

Synthesis of 2-Benzyl-4-methyl-1,1,3-trioxo-1,2,3,4-tetrahydro-1l$^6$-benzo[1,2,4]thiadiazine-7-carboxylic Acid Benzyl Ester Step 1: Synthesis of 4-Methyl-1,1,3-trioxo-1,2,3,4-tetrahydro-1l$^6$-benzo[1,2,4]thiadiazine-7-carboxylic Acid Methyl Ester Methyl-4-methylaminobenzoate (4.96 g, 30 mmoles) was dissolved in 20 mL of nitromethane, and this solution was added dropwise to a solution of 3.13 mL N-chlorosulfonyl isocyanate in 5 mL of nitromethane at 0° C. The resulting solution was stirred for 15 minutes and then 5.2 g (39 mmoles) of solid aluminum trichloride was added. The resulting mixture was heated to reflux for 1 hour. The reaction mixture was concentrated to dryness in vacuo, and the residue was diluted by carefully adding 30 mL of ice water. The resulting yellowish solid was collected by filtration and recrystallized from 30 mL of ethyl acetate to give 3.95 g (49%) of the title compound as an off-white powder. $^1$H-NMR (CDCl$_3$): δ 8.47 (s, 1H), 8.22 (d, 1H), 7.24 (d, 2H), 3.89 (s, 3H), and 3.46 (s, 3H) ppm. MS: M$^+$+1=271.1 Da Step 2: Synthesis of 2-Benzyl-4-methyl-1,1,3-trioxo-1,2,3,4-tetrahydro-1l$^6$-benzo[1,2,4]thiadiazine-7-carboxylic Acid Methyl Ester 4-Methyl-1,1,3-trioxo-1,2,3,4-tetrahydro-1l$^6$-benzo[1,2,3,4]thiadiazine-7-carboxylic acid methyl ester (1.00 g, 3.7 mmoles) was mixed with benzyl bromide (0.66 mL, 5.6 mmoles) in 25 mL of acetonitrile containing 0.83 mL (5.6 mmoles) of 1,8-diazabicyclo[5.4.0]undec-7-ene. The reaction mixture was stirred for 16 hours at room temperature. The mixture was concentrated to 5 mL by evaporation of solvents in vacuo, and the oil was partitioned between 25 mL of 1 M HCl and 25 mL of ethyl acetate. The organic layer was separated, dried (magnesium sulfate), and concentrated to give the product as an off-white solid. The white solid was triturated 3 times with 25 mL portions of hexanes to give 0.98 g (73%) of the title compound. $^1$H-NMR (CDCl$_3$): δ 8.58 (s, 1H), 8.30 (d, 1H), 7.44 (d, 2H), 7.27 (m, 4H), 5.07 (s, 2H), 3.96 (s, 3H), and 3.53 (s, 3H) ppm. Anal. (C$_{17}$H$_{16}$N$_2$O$_5$S$_1$) C,H,N. MS: M$^+$+1=361.0 Da Step 3: Synthesis of 2-Benzyl-4-methyl-1,1,3-trioxo-1,2,3,4-tetrahydro-1l$^6$-benzo[1,2,4]thiadiazine-7-carboxylic Acid.

2-Benzyl-4-methyl-1,1,3-trioxo-1,2,3,4-tetrahydro-1l$^6$-benzo[1,2,4]-thiadiazine-7-carboxylic acid methyl ester (0.87 g, 2.4 mmoles) was mixed with 3 mL of 1 M NaOH in 25 mL of methanol. The reaction mixture was stirred for 60 hours and then concentrated to dryness in vacuo. The residue was partitioned between 20 mL of water and 30 mL dichloromethane. The aqueous layer was acidified with conc. HCl, and the resulting suspension was collected by filtration and dried on the vacuum filter to give 0.60 g (73%) of the title compound as an off-white solid. $^1$H-NMR (CDCl$_3$): δ 8.67 (s, 1H), 8.37 (d, 1H), 7.46 (d, 2H), 7.30 (m, 4H), 5.08 (s, 2H), and 3.56 (s, 3H) ppm. MS: M$^+$+1=347.1 Da Step 4: Synthesis of 2-Benzyl-4-methyl-1,1,3-trioxo-1,2,3,4-tetrahydro-1l$^6$-benzo[1,2,4]thiadiazine-7-carboxylic Acid Benzyl Ester 2-Benzyl-4-methyl-1,1,3-trioxo-1,2,3,4-tetrahydro-1l$^6$-benzo[1,2,4]-thiadiazine-7-carboxylic acid (0.25 g, 0.7 mmoles) was suspended in 20 mL of dichloromethane. Oxalyl chloride (0.076 mL, 0.87 mmoles) was added to the suspension, followed by 2 drops of DMF. The resulting effervescent mixture was stirred for 3 hours. The resulting clear solution was then concentrated to dryness to give an oil. Benzyl alcohol (0.082 mL, 0.79 mmoles) was added to the oil, and the mixture was dissolved in 5 mL of pyridine. 40 mL of water was added, and the resulting milky mixture was stirred for 2 hours. The suspension was filtered and the solid filter cake was chromatographed on silica (eluting with 30% ethyl acetate in hexanes) to give 0.10 g (33%) of the title compound as a white solid. $^1$H-NMR (CDCl$_3$): δ 8.59 (s, 1H), 8.33 (d, 1H), 7.36 (m, 8H), 5.39 (s, 2H), 5.07 (s, 2H), and 3.53 (s, 3H) ppm. Anal. (C$_{23}$H$_{20}$N$_2$O$_5$S$_1$) C,H,N. MS: M$^+$+1=437.1 Da

EXAMPLE 2

Synthesis of 2-Benzyl-4-methyl-1,1,3-trioxo-1,2,3,4-tetrahydro-1l$^6$-benzo[1,2,4]thiadiazine-7-carboxylic Acid Benzylamide 2-Benzyl-4-methyl-1,1,3-trioxo-1,2,3,4-tetrahydro-1l$^6$-benzo[1,2,4]thiadiazine-7-carboxylic acid (0.20 g, 0.6 mmoles, from Example 1, Step 3) was suspended in 20 mL of dichloromethane. Oxalyl chloride (0.06 mL, 0.7 mmoles) was added, followed by 2 drops of DMF. The resulting effervescent mixture was stirred for 3 hours. The resulting clear solution was then concentrated to dryness. The residue was redissolved in 15 mL dichloromethane and 0.063 mL of benzylamine (0.6 mmoles) was added, followed by 0.16 mL (1.2 mmoles) of triethylamine. This mixture was stirred for 16 hours at room temperature, and then partitioned between 1 M HCl and dichloromethane. The organic layer was separated, dried (magnesium sulfate), and concentrated to give an off-white solid. Chromatography of the off-white solid on silica gel gave 0.14 g of the title compound as a white solid. $^1$H-NMR (CDCl$_3$); δ 8.23 (s, 1H), 8.17 (d, 1H), 7.35 (m, 11H), 6.47 (bs, 1H), 5.05 (s, 2H), 4.65 (d, 2H), and 3.52 (s, 3H) ppm. Anal. (C$_{23}$H$_{21}$N$_3$O$_4$S$_1$.0.25H$_2$O) C,H,N. MS: M$^+$+1=436.1 Da

EXAMPLE 3

Synthesis of 2-Benzyl-4-methyl-1,1,3-trioxo-1,2,3,4-tetrahydro-1l$^6$-benzo[1,2,4]thiadiazine-7-carboxylic acid (pyridin-4-ylmethyl)-amide The procedure of Example 2 was followed, except that 4-(aminomethyl) pyridine was substituted for benzylamine, to provide the title compound. $^1$H-NMR (CDCl$_3$); δ 8.59 (d, 2H), 8.29 (s, 1H), 8.21 (d, 1H), 7.42 (d, 2H), 7.30 (m, 6H), 5.06 (s, 2H), 4.67 (d, 2H), and 3.54 (s, 3H) ppm. Anal. (C$_{22}$H$_{20}$N$_4$O$_4$S$_1$.0.5C$_4$H$_8$O$_2$) C,H,N. MS: M$^+$+1=437.1 Da

EXAMPLE 4

Synthesis of 2-Benzyl-4-methyl-1,1,3-trioxo-1,2,3,4-tetrahydro-1l$^6$-benzo[1,2,4]thiadiazine-7-carboxylic acid (1H-indol-5-ylmethyl)-amide The procedure of Example 2 was followed except that 5-(methylamino)indole was substituted for benzylamine, to provide the title compound. $^1$H-NMR (CDCl$_3$); δ 9.43 (bs, 1H), 8.45 (s, 1H), 8.18 (m, 2H), 7.52 (s, 1H), 7.19 (m, 9H), 6.37 (s, 1H), 4.94 (s, 2H), 4.60 (d, 2H), and 3.41 (s, 3H) ppm. Anal. (C$_{25}$H$_{22}$N$_4$O$_4$S$_1$.0.33H$_2$O) C,H,N. MS: M$^+$+1=475.2 Da

EXAMPLE 5

Synthesis of 2-Benzyl-4-methyl-1,1,3-trioxo-1,2,3,4-tetrahydro-1l$^6$-benzo[1,2,4]thiadiazine-7-carboxylic acid 4-methoxy-benzylamide The procedure of Example 2 was followed except that 4-methoxybenzylamine was substituted for benzylamine, to provide the title compound. $^1$H-NMR (CDCl$_3$); δ 8.21 (s, 1H), 8.14 (d, 1H), 7.40 (d, 2H), 7.27 (m, 6H), 6.89 (d, 2H), 6.50 (bs, 1H), 5.04 (s, 2H), 4.57 (d, 2H), 3.80 (s, 3H), and 3.51 (s, 3H) ppm. Anal. (C$_{24}$H$_{23}$N$_3$O$_5$S$_1$) C,H,N. MS: M$^+$+1=466.2 Da

EXAMPLE 6

Synthesis of 2-Benzyl-4-methyl-1,1,3-trioxo-1,2,3,4-tetrahydro-1l$^6$-benzo[1,2,4]thiadiazine-7-carboxylic acid 4-(2-tert-butylsulfamoyl-ethyl)-benzylamide The procedure of Example 2 was followed except that 2-(4-Aminomethyl-phenyl)-ethanesulfonic acid t-butyl amide was substituted for benzylamine, to provide the title compound. $^1$H-NMR (CDCl$_3$); δ 8.20 (m, 2H), 7.30 (m, 12H), 5.05 (s, 2H), 4.60 (d, 2H), 4.30 (t, 2H), 4.07 (t, 2H), 3.24 (s, 3H), and 1.35 (s, 9H) ppm. Anal. (C$_{29}$H$_{34}$N$_4$O$_6$S$_2$.0.75C$_4$H$_{10}$O.0.2CH$_2$Cl$_2$) C,H,N. MS: M$^+$–1=598.1 Da

EXAMPLE 7

Synthesis of 2-Benzyl-4-methyl-1,1,3-trioxo-1,2,3,4-tetrahydro-1l$^6$-benzo[1,2,4]thiadiazine-7-carboxylic acid (1H-indol-2-ylmethyl)-amide The procedure of Example 2 was followed except that C-indol-2-yl-methylamine was substituted for benzylamine, to provide the title compound. $^1$H-NMR (CDCl$_3$); δ 8.95 (s, 1H), 8.25 (s, 1H), 8.09 (d, 1H), 7.54 (d, 2H), 7.40 (d, 2H), 7.24 (m, 6H), 7.07 (t, 1H), 6.95 (t, 1H), 6.38 (s, 1H), 5.04 (s, 2H), 4.70 (d, 2H), and 3.48 (s, 3H) ppm. Anal. (C$_{25}$H$_{22}$N$_4$O$_4$S$_1$.0.5C$_4$H$_{10}$O.0.5H$_2$O) C,H,N. MS: M$^+$+1=475.1 Da

EXAMPLE 8

Synthesis of 2-Benzyl-4-methyl-1,1,3-trioxo-1,2,3,4-tetrahydro-1l$^6$-benzo[1,2,4]thiadiazine-7-carboxylic acid 4-(2-sulfamoyl-ethyl)-benzylamide 2-Benzyl-4-methyl-1,1,3-trioxo-1,2,3,4-tetrahydro-1l$^6$-benzo[1,2,4]thiadiazine-7-carboxylic acid 4-(2-tert-butylsulfamoyl-ethyl)-benzylamide (0.11 g, Example 6) was dissolved in 5 mL of trifluoroacetic acid at room temperature. This solution was stirred for 1 hour, concentrated in vacuo, and quenched with water. The mixture was extracted with ethyl acetate. The ethyl acetate extracts were dried (magnesium sulfate), filtered, and concentrated to give a white foam. Triturated with diethyl ether to give the title compound as a gray solid. $^1$H-NMR (CDCl$_3$); δ 8.20 (m, 2H), 7.28 (m, 12H), 5.05 (s, 2H), 4.64 (d, 2H), 4.29 (t, 2H), 4.06 (t, 2H), 3.23 (s, 3H), and 3.07 (bs, 2H) ppm. Anal. (C$_{25}$H$_{26}$N$_4$O$_6$S$_2$.0.5C$_4$H$_{10}$O.1.H$_2$O) C,H,N. MS: M$^+$–1=543.0 Da

EXAMPLE 9

Synthesis of 2-(4-Methanesulfonyl-benzyl)-4-methyl-1,1,3-trioxo-1,2,3,4-tetrahydro-1l$^6$-benzo[1,2,4]thiadiazine-7-carboxylic Acid Benzylamide Step 1: Synthesis of 2-(4-Methanesulfonyl-benzyl)-4-methyl-1,1,3-trioxo-1,2,3,4-tetrahydro-1λ$^6$-benzo[1,2,4]thiadiazine-7-carboxylic Acid Methyl Ester.

The procedure of Example 1, Step 2 was followed except that 4-methanesulfonyl-benzyl chloride was substituted for benzyl bromide, to provide the title compound. $^1$H-NMR (CDCl$_3$); δ 8.58 (s, 1H), 8.34 (dd, 1H), 7.89 (d, 2H), 7.64 (d, 2H), 7.32 (d, 1H), 5.12 (s, 2H), 3.97 (s, 3H), 3.56 (s, 3H) and 3.02 (s, 3H) ppm. MS: M$^+$+1=439.0 Da Step 2: Synthesis of 2-(4-Methanesulfonyl-benzyl)-4-methyl-1,1,3-trioxo-1,2,3,4-tetrahydro-1λ$^6$-benzo[1,2,4]thiadiazine-7-carboxylic Acid.

2-(4-Methanesulfonyl-benzyl)-4-methyl-1,1,3-trioxo-1,2,3,4-tetrahydro-1$^6$-benzo[1,2,4]thiadiazine-7-carboxylic acid methyl ester was hydrolyzed according to the method described in Example 1, Step 3 to give the title compound. $^1$H-NMR (CDCl$_3$); δ 8.49 (bs, 1H), 8.26 (d, 1H), 7.82 (d, 2H), 7.51 (d, 2H), 7.44 (d, 1H), 5.29 (s, 2H), 3.56 (s, 3H) and 3.02 (s, 3H) ppm. MS: M$^+$–1=423.0 Da Step 3: Synthesis of 2-(4-Methanesulfonyl-benzyl)-4-methyl-1,1,3-trioxo-1,2,3,4-tetrahydro-1$\lambda^6$-benzo[1,2,4]thiadiazine-7-carboxylic Acid Benzylamide 2-(4-Methanesulfonyl-benzyl)-4-methyl-1,1,3-trioxo-1,2,3,4-tetrahydro-1$\lambda^6$-benzo[1,2,4]thiadiazine-7-carboxylic acid was coupled with benzyl amine according to the procedure of Example 2 to give the title compound. $^1$H-NMR (CDCl$_3$); δ 8.19 (s, 1H), 8.01 (d, 1H), 7.74 (d, 2H), 7.45 (d, 2H), 7.34 (m, 6H), 6.67 (bs, 1H), 4.62 (t, 2H), 3.76 (bs, 2H), 3.22 (s, 3H) and 2.98 (s, 3H) ppm. Anal. ($C_{24}H_{23}N_3O_6S_2 \cdot 0.5C_4H_{10}O \cdot 0.66H_2O$) C,H,N. MS: M$^+$+1=514.1 Da

EXAMPLE 10

Synthesis of 4-(7-Benzylcarbamoyl-4-methyl-1,1,3-trioxo-3,4-dihydro-1H-1l$^6$-benzo[1,2,4]thiadiazin-2-ylmethyl)-benzoic Acid Tert-Butyl Ester The procedure of Example 9 was followed except that in Step 2, t-butyl-p-bromomethylbenzoate was substituted for 4-methanesulfonyl-benzyl chloride, to provide the title compound. $^1$H-NMR (CDCl$_3$); δ 8.23 (s, 1H), 8.18 (dd, 1H), 7.90 (d, 2H), 7.44 (d, 2H), 7.32 (m, 6H), 6.53 (t, 1H), 5.07 (s, 2H), 4.65 (d, 2H), 3.52 (s, 3H), and 1.54 (s, 9H) ppm. Anal. ($C_{28}H_{29}N_3O_6S_1$) C,H,N. MS: M$^+$+1=536.2 Da

EXAMPLE 11

Synthesis of 4-(7-Benzylcarbamoyl-4-methyl-1,1,3-trioxo-3,4-dihydro-H-1l$^6$-benzo[1,2,4]thiadiazin-2-ylmethyl)-benzoic Acid 4-(7-Benzylcarbamoyl-4-methyl-1,1,3-trioxo-3,4-dihydro-1H-1$\lambda^6$-benzo[1,2,4]thiadiazin-2-ylmethyl)-benzoic acid tert-butyl ester (0.81 g, Example 10) was dissolved in 4 mL of trifluoroacetic acid. Stirred for 1 hour, concentrated in vacuo, and triturated the residue with diethyl ether to provide the title compound (0.65 g, 90%) as a white solid. $^1$H-NMR (CDCl$_3$); δ 8.49 (s, 1H), 8.27 (dd, 1H), 8.19 (t, 1H), 7.92 (d, 2H), 7.40 (d, 2H), 7.28 (m, 6H), 5.04 (s, 2H), 4.58 (d, 2H), and 3.48 (s, 3H) ppm. Anal. ($C_{24}H_{21}N_3O_6 \cdot 0.25C_4H_{10}O \cdot 0.66H_2O$) C,H,N. MS: M$^+$+1=480.1 Da

EXAMPLE 12

Synthesis of 4-[7-(4-Methoxy-benzylcarbamoyl)-4-methyl-1,1,3-trioxo-3,4-dihydro-1H-1l$^6$-benzo[1,2,4]thiadiazin-2-ylmethyl]-Benzoic Acid Tert-Butyl Ester The procedure of Example 9 was followed except that in Step 2, t-butyl-p-bromomethylbenzoate was substituted for 4-methanesulfonyl-benzyl chloride; and in Step 3, 4-methoxybenzylamine was substituted for benzyl amine, to provide the title compound. $^1$H-NMR (CDCl$_3$); δ 8.21 (s, 1H), 8.17 (dd, 1H), 7.90 (d, 2H), 7.43 (d, 2H), 7.27 (m, 3H), 6.89 (d, 2H), 6.48 (t, 1H), 5.07 (s, 2H), 4.57 (d, 2H), 3.80 (s, 3H), 3.51 (s, 3H), and 1.54 (s, 9H) ppm. Anal. ($C_{29}H_{31}N_3O_7S_1$) C,H,N. MS: M$^+$+1=566.2 Da

EXAMPLE 13

Synthesis of 4-[7-(4-Methoxy-benzylcarbamoyl)-4-methyl-1,1,3-trioxo-3,4-dihydro-1H-1l$^6$-benzo[1,2,4]thiadiazin-2-ylmethyl]-benzoic Acid The procedure of Example 11 was followed except that 4-[7-(4-Methoxy-benzylcarbamoyl)4-methyl-1,1,3-trioxo-3,4-dihydro-1H-1$\lambda^6$-benzo[1,2,4]thiadiazin-2-ylmethyl]-benzoic acid tert-butyl ester (Example 12) was substituted for 4-(7-Benzylcarbamoyl-4-methyl-1,1,3-trioxo-3,4-dihydro-1H-1$\lambda^6$-benzo[1,2,4]thiadiazin-2-ylmethyl)-benzoic acid tert-butyl ester (Example 10) to provide the title compound. $^1$H-NMR (CDCl$_3$); δ 8.45 (s, 1H), 8.22 (m, 2H), 7.89 (d, 2H), 7.37 (d, 2H), 7.23 (m, 3H), 6.79 (d, 2H), 5.00 (s, 2H), 4.47 (d, 2H), 3.71 (s, 3H), and 3.45 (s, 3H) ppm. Anal. ($C_{25}H_{23}N_3O_7S_1 \cdot 0.33H_2O$) C,H,N. MS: M$^+$+1=510.1 Da

EXAMPLE 14

Synthesis of 2-(4-Carbamoyl-benzyl)-4-methyl-1,1,3-trioxo-1,2,3,4-tetrahydro-1l$^6$-benzo[1,2,4]thiadiazine-7-carboxylic acid 4-methoxy-benzylamide 4-[7-(4-Methoxy-benzylcarbamoyl)-4-methyl-1,1,3-trioxo-3,4-dihydro-1H-1$\lambda^6$-benzo[1,2,4]thiadiazin-2-ylmethyl]-benzoic acid (0.1 g, Example 13) was mixed in 10 mL dichloromethane with 0.03 mL of oxalyl chloride. The resulting effervescent solution was stirred for 1 hour and then concentrated in vacuo. The residue was dissolved in 10 mL dichloromethane and added to a mixture of 5 mL ammonium hydroxide in 20 mL diethyl ether. This mixture was stirred for 1 hour and then concentrated in vacuo. The resulting solid was washed with water to give 0.04 g of the title compound as a gray solid. $^1$H-NMR (CDCl$_3$); δ 8.45 (s, 1H), 8.25 (d, 1H), 8.02 (t, 1H), 7.72 (d, 2H), 7.43 (d, 2H), 7.25 (s, 3H), 6.82 (d, 2H), 5.03 (s, 2H), 4.50 (d, 2H), 3.74 (s, 3H), 3.48 (s, 3H), and 2.56 (bs, 2H) ppm. Anal. ($C_{25}H_{24}N_4O_6S_1 \cdot 0.2C_4H_{10}O \cdot 0.25H_2O$) C,H,N. MS: M$^+$+1=509.1 Da

EXAMPLE 15

Synthesis of 2-(4-Methanesulfonyl-benzyl)-4-methyl-1,1,3-trioxo-1,2,3,4-tetrahydro-1l$^6$-benzo[1,2,4]thiadiazine-7-carboxylic acid 4-methoxy-benzylamide The procedure of Example 9 was followed except that in Step 3, 4-methoxybenzylamine was substituted for benzylamine, to provide the title compound. $^1$H-NMR (CDCl$_3$); δ 8.17 (bs, 1H), 8.00 (d, 1H), 7.77 (d, 2H), 7.47 (d, 2H), 7.37 (d, 1H), 7.28 (m, 3H), 6.89 (d, 2H), 6.47 (bt, 1H), 4.56 (m, 2H), 4.36 (m, 1H), 4.13 (m, 1H), 3.80 (s, 3H), 3.24 (s, 3H), and 3.01 (s, 3H) ppm. Anal. ($C_{25}H_{25}N_3O_7S_2 \cdot 0.5C_4H_{10}O \cdot 1.5H_2O$) C,H,N. MS: M$^+$+1=544.1 Da

EXAMPLE 16

Synthesis of 2-Benzyl-4-methyl-1,1,3-trioxo-1,2,3,4-tetrahydro-1l$^6$-benzo[1,2,4]thiadiazine-7-carboxylic acid 4-fluoro-benzylamide The procedure of Example 2 was followed except that 4-fluorobenzylamine was substituted for benzylamine, to provide the title compound. $^1$H-NMR (CDCl$_3$); δ 8.21 (s, 1H), 8.15 (dd, 1H), 7.40 (d, 2H), 7.29 (m, 6H), 7.04 (t, 2H), 6.57 (t, 1H), 5.04 (s, 2H), 4.60 (d, 2H), and 3.51 (s, 3H) ppm. Anal. ($C_{23}H_{20}N_3O4S_1F_1$) C,H,N. MS: M$^+$+1=454.2 Da

EXAMPLE 17

Synthesis of 4-Methyl-2-(4-nitro-benzyl)-1,1,3-trioxo-1,2,3,4-tetrahydro-1l$^6$-benzo[1,2,4]thiadiazine-7-carboxylic acid 4-methoxy-benzylamide Step 1: Synthesis of 4-Methyl-1,1,3-trioxo-1,2,3,4-tetrahydro-1$\lambda^6$-benzo[1,2,4]thiadiazine-7-carboxylic Acid.

4-Methyl-1,1,3-trioxo-1,2,3,4-tetrahydro-1$\lambda^6$-benzo[1,2,4]thiadiazine-7-carboxylic acid methyl ester (10.0 g, Example 1, Step 1) was dissolved in 200 ML of methanol with 75 mL of 1M NaOH. Stirred for 4 hours and concentrated in vacuo to remove the methanol. The residue was acidified with concentrated HCl, filtered, and washed with water. Air dried on the vacuum filter to give 9.5 g of the title compound as a tan solid. $^1$H-NMR (DMSO-d$_6$); δ 8.04 (s, 1H), 7.94 (dd, 1H), and 7.17 (d, 1H) ppm. MS: M$^+$−1=255.1 Da Step 2: Synthesis of 4-Methyl-1,1,3-trioxo-1,2,3,4-tetrahydro-1$\lambda^6$, benzo[1,2,4]thiadiazine-7-carboxylic acid 4-methoxy-benzylamide.

4-Methyl-1,1,3-trioxo-1,2,3,4-tetrahydro-1$\lambda^6$-benzo[1,2,4]thiadiazine-7-carboxylic acid (2.5 g, Step 1) was mixed with 4-methoxybenzylamine (1.32 g) and 1-hydroxybenzotriazole in 50 mL of N,N-dimethylformamide. 1-(3-Dimethylaminopropyl)-3-ethylcarbodiimide hydrochloride (1.87 g) was added, and the mixture was allowed to stir at room temperature for 16 hours. The reaction was partitioned between 1M HCl and ethyl acetate. The organic layer was extracted with saturated sodium bicarbonate. The bicarbonate layer was then acidified and filtered. The white solid was washed with diethyl ether to give the title compound (2.26 g). $^1$H-NMR (CDCl$_3$); δ 9.25 (t, 1H), 8.35 (d, 1H), 8.21 (dd, 1H), 7.57 (d, 1H), 7.22 (d, 2H), 6.86 (dd, 2H), 4.39 (d, 2H), 3.69 (s, 3H), 3.42 (s, 3H) and 2.47 (bs, 1H) ppm. MS: M$^+$+1=376.1 Da Step 3: Synthesis of 4-Methyl-2-(4-nitro-benzyl)-1,1,3-trioxo-1,2,3,4-tetrahydro-1$\lambda^6$-benzo[1,2,4]thiadiazine-7-carboxylic acid 4-methoxy-benzylamide.

4-Methyl-1,1,3-trioxo-1,2,3,4-tetrahydro-1$\lambda^6$-benzo[1,2,4]thiadiazine-7-carboxylic acid 4-methoxy-benzylamide (1.0 g), and cesium carbonate (0.87 g) were mixed in 50 mL of N,N-dimethylformamide. 4-Nitrobenzylbromide (0.58 g) was added, and the resulting mixture was stirred for 16 hours at room temperature. The reaction was diluted with 1M HCl and filtered to give a gummy solid. Recrystallization from ethyl alcohol gave the title compound as a white solid (0.77 g). $^1$H-NMR (CDCl$_3$); δ 8.48 (s, 1H), 8.26 (d, 1H), 8.10 (m, 3H), 7.54 (d, 2H), 7.25 (m, 4H), 6.82 (t, 2H), 5.05 (s, 2H), 4.50 (d, 2H), 3.73 (d, 3H), and 3.48 (s, 3H) ppm. Anal. (C$_{24}$H$_{22}$N$_4$O$_7$S-1.01H$_2$O) C,H,N. MS: M$^+$+1=511.2 Da

EXAMPLE 18

Synthesis of 4-Methyl-2-(4-methylsulfamoyl-benzyl)-1,1,3-trioxo-1,2,3,4-tetrahydro-11$^6$-benzo[1,2,4]thiadiazine-7-carboxylic acid 4-methoxy-benzylamide The procedure of Example 17 was followed except that in Step 3, 4-methylsulfamoyl-benzyl bromide was substituted for 4-nitrobenzylbromide, to provide the title compound. $^1$H-NMR (CDCl$_3$); δ 8.23 (d, 1H), 8.18 (d, 1H), 7.76 (d, 2H), 7.55 (d, 2H), 7.27 (m, 4H), 6.89 (d, 2H), 6.48 (bt, 1H), 5.08 (s, 2H), 4.58 (d, 2H), 3.80 (s, 3H), 3.54 (s, 3H), and 2.62 (d, 3H) ppm. Anal. (C$_{25}$H$_{26}$N$_4$O$_7$S$_2$.0.66C$_2$H$_6$O) C,H,N. MS: M$^+$+1=559.1 Da

EXAMPLE 19

Synthesis of 4-Methyl-2-[4-(morpholine-4-sulfonyl)-benzyl]-1,1,3-trioxo-1,2,3,4-tetrahydro-11$^6$-benzo[1,2,4]thiadiazine-7-carboxylic acid 4-methoxy-benzylamide The procedure of Example 17 was followed except that in Step 3, 4-(4-bromomethyl-benzenesulfonyl)-morpholine was substituted for 4-nitrobenzylbromide, to provide the title compound. $^1$H-NMR (CDCl$_3$); δ 8.25 (s, 1H), 8.18 (d, 1H), 7.66 (d, 2H), 7.58 (d, 2H), 7.29 (m, 4H), 6.88 (d, 2H), 6.54 (bt, 1H), 5.08 (s, 2H), 4.57 (d, 2H), 3.80 (s, 3H), 3.69 (s, 4H), 3.54 (s, 3H), and 2.94 (s, 4H) ppm. Anal. (C$_{28}$H$_{30}$N$_4$O$_8$S$_2$.0.66H$_2$O) C,H,N. MS: M$^+$+1=615.2Da

EXAMPLE 20

Synthesis of 4-[7-(4-Fluoro-benzylcarbamoyl)-4-methyl-1,1,3-trioxo-3,4-dihydro-1H-11$^6$-benzo[1,2,4]thiadiazin-2-ylmethyl]-benzoic Acid Methyl Ester The procedure of Example 17 was followed except that in Step 2, 4-fluorobenzyl amine was substituted for 4-methoxybenzylamine and in Step 3, methyl-4-bromomethylbenzoate was substituted for 4-nitrobenzylbromide, to provide the title compound. $^1$H-NMR (CDCl$_3$); δ 8.24 (s, 1H), 8.19 (d, 1H), 7.94 (d, 2H), 7.45 (d, 2H), 7.29 (m, 3H), 7.03 (t, 2H), 6.71 (bt, 1H), 5.07 (s, 2H), 4.60 (d, 2H), 3.87 (s, 3H), and 3.52 (s, 3H) ppm. Anal. (C$_{25}$H$_{22}$N$_3$O$_6$S$_1$F$_1$) C,H,N. MS: M$^+$+1=512.2 Da

EXAMPLE 21

Synthesis of 2-Benzyl-4-methyl-1,1,3-trioxo-1,2,3,4-tetrahydro-11$^6$-benzo[1,2,4]thiadiazine-7-carboxylic acid (2-methoxy-pyridin-4-ylmethyl)-amide The procedure of Example 2 was followed except that C-(2-Methoxy-pyridin-4-yl)-methylamine was substituted for benzylamine, to provide the title compound. $^1$H-NMR (CDCl$_3$); δ 8.26 (s, 1H), 8.18 (d, 1H), 8.13 (d, 1H), 7.43 (d, 2H), 7.30 (m, 4H), 6.84 (d, 1H), 6.69 (s, 2H), 5.06 (s, 2H), 4.61 (d, 2H), 3.93 (s, 3H), and 3.53 (s, 3H) ppm. Anal. (C$_{23}$H$_{22}$N$_4$O$_5$S$_1$) C,H,N. MS: M$^+$+1=467.2 Da

EXAMPLE 22

Synthesis of 4-Methyl-2-naphthalen-2-ylmethyl-1,1,3-trioxo-1,2,3,4-tetrahydro-11$^6$-benzo[1,2,4]thiadiazine-7-carboxylic acid 4-methoxy-benzylamide The procedure of Example 17 was followed except that in Step 3, 2-Bromomethyl-naphthalene was substituted for 4-nitrobenzylbromide, to provide the title compound. Anal. (C$_{28}$H$_{25}$N$_3$O$_5$S$_1$) C,H,N. MS: M$^+$+1=516.3 Da

EXAMPLE 23

Synthesis of 2-Biphenyl-4-ylmethyl-4-methyl-1,1,3-trioxo-1,2,3,4-tetrahydro-11$^6$-benzo[1,2,4]thiadiazine-7-carboxylic acid 4-methoxy-benzylamide The procedure of Example 17 was followed except that in Step 3, 4-Bromomethyl-biphenyl was substituted for 4-nitrobenzylbromide, to provide the title compound. Anal. (C$_{28}$H$_{25}$N$_3$O$_5$S$_1$) C,H,N. MS: M$^+$+1=541.0 Da

EXAMPLE 24

Synthesis of 2-Benzyl-4-methyl-1,1,3-trioxo-1,2,3,4-tetrahydro-11$^6$-benzo[1,2,4]thiadiazine-7-carboxylic acid (2,1,3-benzothiadiazol-5-ylmethyl)-amide The procedure of Example 2 was followed except that C-Benzo[1,2,5]thiadiazol-5-yl-methylamine hydrochloride was substituted for benzylamine, to provide the title compound. $^1$H-NMR (CDCl$_3$); δ 8.28 (s, 1H), 8.19 (dd, 1H), 7.98 (d, 1H), 7.92 (s, 1H), 7.58 (d, 1H), 7.41 (dd, 2H), 7.28 (m, 4H), 6.86 (bt, 1H), 5.05 (s, 2H), 4.83 (d, 2H), and 3.52 (s, 3H) ppm. Anal. (C$_{23}$H$_{19}$N$_5$O$_4$S$_2$) C,H,N. MS: M$^+$+1=494.2 Da

EXAMPLE 25

Synthesis of 4-[7-(4-Fluoro-benzylcarbamoyl)-4-methyl-1,1,3-trioxo-3,4-dihydro-1H-11$^6$-benzo[1,2,4]thiadiazin-2-ylmethyl]-benzoic Acid The procedure of Example 17 was followed except that in Step 2, 4-fluorobenzyl amine was substituted for 4-methoxybenzylamine and in Step 3, 4-bromomethyl-benzoic acid tert-butyl ester was substituted for 4-nitrobenzylbromide. The resulting t-butyl ester intermediate was hydrolyzed following the procedure set forth in Example 11 to provide the title compound. $^1$H-NMR (CDCl$_3$); δ 8.54 (bt, 1H), 8.50 (s, 1H), 8.26 (dd, 1H), 7.89 (d, 2H), 7.38 (d, 2H), 7.26 (m, 3H), 6.94 (t, 2H), 5.01 (s, 2H), 4.50 (d, 2H), and 3.46 (s, 3H) ppm. Anal. (C$_{24}$H$_{20}$N$_3$O$_6$S$_1$F$_1$.H$_2$O) C,H,N. MS: M$^+$+1=498.2 Da

EXAMPLE 26

Synthesis of 4-[7-(4-Methoxy-benzylcarbamoyl)-4-methyl-1,1,3-trioxo-3,4-dihydro-1H-11$^6$-benzo[1,2,4]thiadiazin-2-ylmethyl]-benzoic acid 2-dimethylamino-ethyl Ester Hydrochloride To a mixture of 0.39 (0.77 mmol) 4-[7-(4-Methoxy-benzylcarbamoyl)-4-methyl-1,1,3-trioxo-3,4-dihydro-1H-1$\lambda^6$-benzo[1,2,4]thiadiazin-2-ylmethyl]-benzoic acid (Example 13), 1-(3-dimethylaminopropyl)-3-ethylcarbodiimide hydrochloride ("EDAC-HCl") 0.19 g (0.99 mmol), 1-hydroxybenzotriazole monohydrate ("HOBT") 0.13 g (0.99 mmol), in dimethylformamide (5 mL) is added 2-N,N-dimethyl ethanolamine 0.089 g (0.99 mmol). The mixture is stirred overnight at room temperature before adding water (20 μL) and extracting with ethyl acetate (2×20 mL). Combined organic layers and wash with saturated aqueous NaCl, dry MgSO$_4$. Concentrate, dissolve in methanol and treat with 1 M HCl in ether. Concentrate, and slurry in hot ethyl acetate. Slurried product in hot ethyl acetate to obtain 0.27 g of the title compound. Anal. ($C_{29}H_{32}N_4O_7S_1$HCl 1.29H$_2$O) C,H,N. MS: M$^+$+1=581.4 Da

EXAMPLE 27

Synthesis of 4-Methyl-1,1,3-trioxo-2-[4-(piperidine-1-carbonyl)-benzyl]-1,2,3,4-tetrahydro-1l$^6$-benzo[1,2,4]thiadiazine-7-carboxylic acid 4-methoxy-benzylamide Employing the procedure of Example 14 but substituting piperidine for ammonium hydroxide provided the title compound. Anal. ($C_{30}H_{32}N_4O_6S$ 1) C,H,N. MS: M$^+$+1=577.4 Da

EXAMPLE 28

Synthesis of 2-{4-[7-(4-Methoxy-benzylcarbamoyl)-4-methyl-1,1,3-trioxo-3,4-dihydro-1l$^6$-benzo[1,2,4]thiadiazin-2-ylmethyl]-benzoylamino}-3-methyl-butyric Acid Step 1: Synthesis of 2-{4-[7-(4-Methoxy-benzylcarbamoyl)-4-methyl-1,1,3-trioxo-3,4-dihydro-1$\lambda^6$-benzo[1,2,4]thiadiazin-2-ylmethyl]-benzoylamino}-3-methyl-butyric Acid Tert Butyl Ester.

Employing the procedure of Example 26 but substituting tert-butyl valine HCl for 2-N,N-dimethyl ethanolamine provided the title compound. MS: M$^+$+1=665.4 Da Step 2: Synthesis of 2-{4-[7-(4-Methoxy-benzylcarbamoyl)-4-methyl-1,1,3-trioxo-3,4-dihydro-1$\lambda^6$-benzo[1,2,4]thiadiazin-2-ylmethyl]-benzoylamino}-3-methyl-butyric Acid.

To a solution of 0.18 g 2-{4-[7-(4-Methoxy-benzylcarbamoyl)-4-methyl-1,1,3-trioxo-3,4-dihydro-1l$^6$-benzo[1,2,4]thiadiazin-2-ylmethyl]-benzoylamino}-3-methyl-butyric acid tert butyl ester (0.27 mmol, Step 1) was added 10 mL 50% trifluoroacetic acid in CHCl$_3$ The resulting mixture was stirred 2 hours at room temperature, then concentrated. Obtained 0.14 g of the title compound as a solid from EtOAc/hexane. Anal. ($C_{30}H_{32}N_4O_8S_1$) C,H,N. MS: M$^+$+1=609.4 Da

EXAMPLE 29

Synthesis of 2-(4-Cyano-benzyl)-4-methyl-1,1,3-trioxo-1,2,3,4-tetrahydro-1l$^6$-benzo[1,2,4]thiadiazine-7-carboxylic acid 4-methoxy-benzylamide The procedure of Example 17 was followed except that in Step 3, 4-Bromomethyl-benzonitrile was substituted for 4-nitrobenzylbromide, to provide the title compound. $^1$H-NMR (CDCl$_3$); δ 8.24 (s, 1H), 8.18 (dd, 1H), 7.59 (dd, 2H), 7.53 (d, 2H), 7.29 (m, 3H), 6.89 (dd, 2H), 6.49 (bt, 1H), 5.06 (s, 2H), 4.58 (d, 2H), 3.81 (s, 3H), and 3.53 (s, 3H) ppm. Anal. ($C_{25}H_{22}N_4O_5S_1$) C,H,N. MS: M$^+$+1=491.3 Da

EXAMPLE 30

Synthesis of {4-[7-(4-Methoxy-benzylcarbamoyl)-4-methyl-1,1,3-trioxo-3,4-dihydro-1H-1l$^6$-benzo[1,2,4]thiadiazin-2-ylmethyl]-phenyl}-acetic Acid The procedure of Example 17 was followed except that in Step 3, (4-Bromomethyl-phenyl)-acetic acid tert-butyl ester was substituted for 4-nitrobenzylbromide. The resulting t-butyl ester intermediate was hydrolyzed following the procedure set forth in Example 11 to provide the title compound. $^1$H-NMR (CDCl$_3$); δ 8.21 (s, 1H), 8.13 (dd, 1H), 7.36 (d, 2H), 7.26 (m, 3H), 7.18 (d, 2H), 6.87 (d, 2H), 6.73 (bt, 1H), 5.02 (s, 2H), 4.54 (d, 2H), 3.79 (s, 3H), 3.58 (s, 2H), and 3.50 (s, 3H) ppm. Anal. ($C_{26}H_{25}N_3O_7S_1$.2H$_2$O) C,H,N. MS: M$^+$+1=524.2 Da

EXAMPLE 31

Synthesis of 4-[7-(3-Methoxy-benzylcarbamoyl)-4-methyl-1,1,3-trioxo-3,4-dihydro-1H-1l$^6$-benzo[1,2,4]thiadiazin-2-ylmethyl]-benzoic Acid The procedure of Example 17 was followed except that in Step 2, 3-methoxy-benzylamine was substituted for 4-methoxybenzylamine and in Step 3, 4-bromomethyl-benzoic acid tert-butyl ester was substituted for 4-nitrobenzylbromide. The resulting t-butyl ester intermediate was hydrolyzed following the procedure set forth in Example 11 to provide the title compound. $^1$H-NMR (CDCl$_3$); δ 8.50 (s, 1H), 8.47 (bt, 1H), 8.25 (dd, 1H), 7.88 (d, 2H), 7.37 (d, 2H), 7.23 (d, 1H), 7.16 (t, 1H) 6.87 (d, 1H), 6.83 (s, 1H), 6.72 (dd, 1H), 5.00 (s, 2H), 4.50 (d, 2H), 3.71 (s, 3H), and 3.45 (s, 3H) ppm. Anal. ($C_{25}H_{23}N_3O_7S$ $_1$.0.25H$_2$O) C,H,N. MS: M$^+$+1=510.2 Da

EXAMPLE 32

Synthesis of 4-Methyl-1,1,3-trioxo-2-[4-(2H-tetrazol-5-yl)-benzyl]-1,2,3,4-tetrahydro-1l$^6$-benzo[1,2,4]thiadiazine-7-carboxylic acid 4-methoxy-benzylamide The procedure of Example 17 was followed except that in Step 3, 5-(4-Bromomethyl-phenyl)-2-trityl-2H-tetrazole was substituted for 4-nitrobenzylbromide. The trityl product was then hydrolyzed in manner similar to the t-butyl hydrolysis set forth in Example 11 to provide the title compound. $^1$H-NMR (DMSO-d$_6$); δ 9.27 (bt, 1H), 8.43 (s, 1H), 8.28 (d, 1H), 7.95 (d, 2H), 7.66 (d, 1H), 7.53 (d, 2H), 7.22 (d, 2H) 6.86 (d, 2H), 5.06 (s, 2H), 4.39 (d, 2H), 3.68 (s, 3H), and 3.49 (s, 3H) ppm. Anal. ($C_{25}H_{23}N_7O_5S$ $_1$.0.66H$_2$O) C,H,N. MS: M$^+$+1=534.2 Da

EXAMPLE 33

Synthesis of 2-(4-Amino-benzyl)-4-methyl-1,1,3-trioxo-1,2,3,4-tetrahydro-1l$^6$-benzo[1,2,4]thiadiazine-7-carboxylic acid 4-methoxy-benzylamide 4-Methyl-2-(4-nitro-benzyl)-1,1,3-trioxo-1,2,3,4-tetrahydro-1$\lambda^6$-benzo[1,2,4]thiadiazine-7-carboxylic acid 4-methoxy-benzylamide (0.6 g, Example 17) was dissolved in 25 mL of glacial acetic acid at room temperature. Powdered zinc (0.77 g) was added in portions and the resulting green mixture was stirred for 2 hours. The reaction was filtered through a pad of Celite, and the solids were washed with ethyl acetate. The filtrate was concentrated to dryness, and the residue was partitioned between 1M sodium hydroxide and ethyl acetate. The organic layer was dried (magnesium sulfate), filtered, and concentrated to give an orange solid. Chromatography (silica, 50% ethyl acetate/hexanes) provide 0.18 g of the title compound. $^1$H-NMR (CDCl$_3$); δ 8.22 (s, 1H), 8.18 (d, 1H), 7.79 (d, 1H), 7.54 (d, 2H), 7.28 (m, 5H) 6.90 (d, 2H), 6.40 (bt, 1H), 5.11 (s, 2H), 4.58 (d, 2H), 3.81 (s, 3H), 3.53 (s, 3H), and 1.56 (bs, 2H) ppm. Anal. ($C_{24}H_{24}N_4O_5S_1$) C,H,N. MS: M$^+$+1=481.2 Da

EXAMPLE 34

Synthesis of 2-Benzyl-4-methyl-1,1,3-trioxo-1,2,3,4-tetrahydro-1l$^6$-benzo[1,2,4]thiadiazine-7-carboxylic acid 3-methoxy-benzylamide The procedure of Example 2 was followed except that 3-methoxybenzylamine was substituted for benzylamine, to provide the title compound. $^1$H-NMR (CDCl$_3$); δ 8.24 (s, 1H), 8.17 (dd, 1H), 7.42 (d, 2H), 7.28 (m, 5H), 6.90 (m, 3H), 6.51 (bs, 1H), 5.06 (s, 2H), 4.62 (d, 2H), 3.81 (s, 3H), and 3.52 (s, 3H) ppm. Anal. (C$_{24}$H$_{23}$N$_3$O$_5$S$_1$) C,H,N. MS: M$^+$+1=466.1 Da

EXAMPLE 35

4-methyl-1,1,3-trioxo-2-pent-2-ynyl-1,2,3,4-tetrahydro-1l$^6$-benzo[1,2,4]thiadiazine-7-carboxylic Acid 4-methoxy-benzylamide In an 8 mL screw cap vial was added a solution of 4-methyl-1,1,3-trioxo-1,2,3,4-tetrahydro-1l$^6$-benzo[1,2,4]thiadiazine-7-carboxylic acid 4-methoxy-benzylamide (0.037 g, 0.1 mmol) in dimethylformamide (1 mL), a solution of 1-Chloro-pent-2-yne (0.023 g, 0.23 mmol) in dimethylformamide (575 mL) and anhydrous cesium carbonate (0.075 g, 0.023 mmol). The vial was capped, and the reaction mixture was shaken for 24 hours at room temperature. The reaction mixture was filtered, and the solvent was removed under vacuum. Purification was carried out via reverse-phase HPLC (3% n-propanol in acetonitrile and 3% n-propanol in water as the eluent; C-18 column) 0.027 g (60% yield).

MS-APCI: M+1=442.1.

In a manner similar to the procedure of Example 35, the compounds of Examples 36 to 47 were prepared.

EXAMPLE 36

4-Methyl-1,1,3-trioxo-2-(1-phenyl-ethyl)-1,2,3,4-tetrahydro-1l$^6$-benzo[1,2,4]thiadiazine-7-carboxylic Acid 4-methoxy-benzylamide

MS-APCI (M+1): 480.5545

EXAMPLE 37

2-(5-Cyano-pentyl)-4-methyl-1,1,3-trioxo-1,2,3,4.tetrahydro-1l$^6$-benzo[1,2,4]thiadiazine-7-carboxylic Acid 4-methoxy-benzylamide

MS-APCI (M+1): 471.5474

EXAMPLE 38

2-(E)-But-2-enyl-4-methyl-1,1,3-trioxo-1,2,3,4-tetrahydro-1l$^6$-benzo[1,2,4]thiadiazine-7-carboxylic Acid 4-methoxy-benzylamide

MS-APCI (M+1): 430.4947

EXAMPLE 39

4-Methyl-1,1,3-trioxo-2-(E)-pent-2-enyl-1,2,3,4-tetrahydro-1l$^6$-benzo[1,2,4]thiadiazine-7-carboxylic Acid 4-methoxy-benzylamide

MS-APCI (M+1): 444.5215

EXAMPLE 40

4-Methyl-2-(2-methyl-allyl)-1,1,3-trioxo-1,2,3,4-tetrahydro-1l$^6$-benzo[1,2,4]thiadiazine-7-carboxylic Acid 4-methoxy-benzylamide

MS-APCI (M+1): 430.4947

EXAMPLE 41

4-Methyl-2-(3-methyl-but-2-enyl)-1,1,3-trioxo-1,2,3,4-tetrahydro-1l$^6$-benzo[1,2,4]thiadiazine-7-carboxylic Acid 4-methoxy-benzylamide

MS-APCI (M+1): 444.5215

EXAMPLE 42

4-Methyl-1,1,3-trioxo-2-[2-(toluene-4-sulfonyl)-ethyl]-1,2,3,4-tetrahydro-1l$^6$-benzo[1,2,4]thiadiazine-7-carboxylic Acid 4-methoxy-benzylamide

MS-APCI (M+1): 558.6453

EXAMPLE 43

2-[$^3$-(4-Fluoro-phenyl)-3-oxo-propyl]-4-methyl-1,1,3-trioxo-1,2,3,4-tetrahydro-1l$^6$-benzo[1,2,4]thiadiazine-7-carboxylic Acid 4-methoxy-benzylamide

MS-APCI (M+1): 526.5546

EXAMPLE 44

4-Methyl-1,1,3-trioxo-2-{2-[(1-phenyl-methanoyl)-amino]-ethyl}-1,2,3,4-tetrahydro-1l$^6$-benzo[1,2,4]thiadiazine-7-carboxylic Acid 4-methoxy-benzylamide

MS-APCI (M+1): 523.5794

EXAMPLE 45

2-Benzo[1,2,5]oxadiazol-5-ylmethyl-4-methyl-1,1,3-trioxo-1,2,3,4-tetrahydro-1l$^6$-benzo[1,2,4]thiadiazine-7-carboxylic Acid 4-methoxy-benzylamide

MS-APCI (M+1): 508.5249

EXAMPLE 46

{5-[7-(4-Methoxy-benzylcarbamoyl)-4-methyl-1,1,3-trioxo-3,4-dihydro-1H-1l$^6$-benzo[1,2,4]thiadiazin-2-ylmethyl]-isoxazol-3-yl}-carbamic Acid Methyl Ester

MS-APCI (M+1): 530.5277

EXAMPLE 47

4-Methyl-1,1,3-trioxo-2-thiazol-4-ylmethyl-1,2,3,4-tetrahydro-1l$^6$-benzo[1,2,4]thiadiazine-7-carboxylic Acid 4-methoxy-benzylamide

MS-APCI (M+1): 473.544

The invention compounds of Formula I have been evaluated in standard assays for their ability to inhibit the catalytic activity of various MMP enzymes. The assays used to evaluate the biological activity of the invention compounds are well-known and routinely used by those skilled in the study of MMP inhibitors and their use to treat clinical conditions.

The assays measure the amount by which a test compound reduces the hydrolysis of a thiopeptolide substrate catalyzed by a matrix metalloproteinase enzyme. Such assays are described in detail by Ye et al., in *Biochemistry*, 1992;31 (45):11231–11235, which is incorporated herein by reference.

Thiopeptolide substrates show virtually no decomposition or hydrolysis at or below neutral pH in the absence of a matrix metalloproteinase enzyme. A typical thiopeptolide substrate commonly utilized for assays is Ac-Pro-Leu-Gly-thioester-Leu-Leu-Gly-OEt. A 100 µL assay mixture will contain 50 mM of N-2-hydroxyethylpiperazine-N'-2-ethanesulfonic acid buffer ("HEPES," pH 7.0), 10 mM CaCl$_2$, 100 µM thiopeptolide substrate, and 1 mM 5,5'-dithio-bis-(2-nitro-benzoic acid) (DTNB). The thiopeptolide substrate concentration may be varied from, for example, 10 to 800 AM to obtain Km and Kcat values. The change in absorbance at 405 nm is monitored on a Thermo Max microplate reader (Molecular Devices, Menlo Park, Calif.) at room temperature (22° C.). The calculation of the amount of hydrolysis of the thiopeptolide substrate is based on $E_{412}$=13600 M$^{-1}$ cm$^{-1}$ for the DTNB-derived product 3-carboxy-4-nitrothiophenoxide. Assays are carried out with and without matrix metalloproteinase inhibitor compounds, and the amount of hydrolysis is compared for a determination of inhibitory activity of the test compounds.

Several representative compounds have been evaluated for their ability to inhibit various matrix metalloproteinase enzymes. Tables 1 and 2 below present inhibitory activity for compounds from this invention. In Table 1 and Table 2, MMP-1FL refers to full-length interstitial collagenase; MMP-2FL refers to full-length Gelatinase A; MMP-3CD refers to the catalytic domain of stromelysin-1; MMP-7FL refers to full-length matrilysin; MMP-9FL refers to full-length Gelatinase B; MMP-13CD refers to the catalytic domain of collagenase 3; and MMP-14CD refers to the catalytic domain of MMP-14. Test compounds were evaluated at various concentrations in order to determine their respective $IC_{50}$ values, the micromolar concentration of compound required to cause a 50% inhibition of the catalytic activity of the respective enzyme.

It should be appreciated that the assay buffer used with MMP-3CD was 50 mM of N-morpholinoethane sulfonate ("MES") at pH 6.0 rather than the HEPES buffer at pH 7.0 described above.

TABLE 1

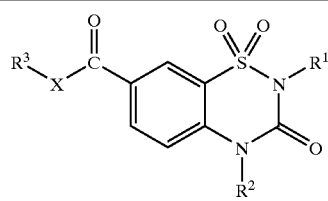

| Ex. No. | $R^1$ | $R^2$ | X | $R^3$ | MMP01 (FL) $IC_{50}, \mu M$ | MMP02 (CD) $IC_{50}, \mu M$ | MMP02 (FL) $IC_{50}, \mu M$ | MMP03 (CD) $IC_{50}, \mu M$ | MMP07 (FL) $IC_{50}, \mu M$ | MMP09 (FL) $IC_{50}, \mu M$ | MMP13 (CD) $IC_{50}, \mu M$ | MMP14 (CD) $IC_{50}, \mu M$ |
|---|---|---|---|---|---|---|---|---|---|---|---|---|
| 1 | $CH_2Ph$ | $CH_3$ | O | $CH_2Ph$ | >100 | >100 | >100 | 85 | 44 | >100 | 0.2 | >100 |
| 2 | $CH_2Ph$ | $CH_3$ | NH | $CH_2Ph$ | >100 | >30 | >30 | >30 | >30 | >30 | 0.88 | >30 |
| 3 | $CH_2Ph$ | $CH_3$ | NH | $CH_2$-4-Py | — | — | — | — | — | — | 0.51 | — |

"—" means not tested.

The inhibition activities of the compounds of Examples 4 to 47 are shown low in Table 2.

TABLE 2

$IC_{50}$ ($\mu M$) Versus Certain MMPs

| Example No. | MMP01 (FL) | MMP02 (FL) | MMP03 (CD) | MMP07 (FL) | MMP09 (FL) | MMP13 (CD) | MMP14 (CD) |
|---|---|---|---|---|---|---|---|
| 4 | —a | — | — | — | — | >30 | — |
| 5 | >30 | >100 | >30 | 51 | >30 | 0.17 | >30 |
| 6 | — | — | — | — | — | >30 | — |
| 7 | — | — | — | — | — | >30 | — |
| 8 | — | — | — | — | — | 63 | — |
| 9 | — | — | — | — | — | 30 | — |
| 10 | — | — | — | — | — | >30 | — |
| 11 | >100 | >100 | >100 | >100 | >100 | 0.066 | >100 |
| 12 | — | — | — | — | — | >30 | — |
| 13 | >100 | >100 | 64 | >100 | >100 | 0.011 | >100 |
| 14 | >30 | — | >100 | >30 | >30 | 0.155 | >30 |
| 15 | — | — | — | — | — | 11 | — |
| 16 | >100 | — | >100 | >30 | >30 | 0.345 | >30 |
| 17 | >30 | — | 16 | >30 | >30 | 0.615 | >30 |
| 18 | >30 | — | 10 | >30 | >30 | 0.31 | >30 |
| 19 | >30 | — | 11 | >30 | >30 | 0.23 | >30 |
| 20 | >30 | — | >30 | >30 | 10 | 0.385 | >30 |
| 21 | >30 | — | >30 | >30 | >30 | 0.155 | >100 |
| 22 | >30 | — | >30 | >30 | >30 | 0.62 | >30 |
| 23 | — | — | — | — | — | >30 | — |
| 24 | >30 | — | 13 | >30 | >30 | 0.125 | >30 |
| 25 | >100 | — | >30 | >100 | >100 | 0.019 | >100 |
| 26 | — | — | — | — | — | 2.2 | — |
| 27 | >30 | — | 10 | >30 | >30 | 0.29 | >30 |
| 28 | >100 | — | >30 | >100 | >100 | 0.25 | >100 |
| 29 | >30 | — | 9.4 | >30 | >30 | 0.13 | >30 |
| 30 | >100 | — | >30 | 82 | >100 | 0.0355 | >100 |
| 31 | >100 | — | >30 | >30 | >100 | 0.00485 | >100 |
| 32 | >100 | — | 15 | >30 | >100 | 0.0062 | >100 |
| 33 | — | — | — | — | — | 8.8 | — |
| 34 | >30 | — | >100 | >30 | >30 | 0.0625 | >30 |
| 35 | — | — | — | — | — | 1.4 | — |
| 36 | — | — | — | — | — | 6.3 | — |
| 37 | — | — | — | — | — | 3.2 | — |
| 38 | — | — | — | — | — | 2.2 | — |
| 39 | — | — | — | — | — | 1.5 | — |
| 40 | — | — | — | — | — | 1.7 | — |
| 41 | — | — | — | — | — | 1.9 | — |
| 42 | — | — | — | — | — | 100 | — |
| 43 | — | — | — | — | — | 30 | — |
| 44 | — | — | — | — | — | 86 | — |
| 45 | — | — | — | — | — | 0.7 | — |
| 46 | — | — | — | — | — | 1.7 | — |
| 47 | — | — | — | — | — | 13 | — | a "—" means data not available.

The foregoing data in Tables 1 and 2 establish that the invention compounds of Formula I are potent inhibitors of MMP enzymes, and are especially useful due to their selective inhibition of MMP-13. Because of this potent and selective inhibitory activity, the invention compounds are especially useful to treat diseases mediated by the MMP enzymes, and particularly those mediated by MMP-13.

Administration of a compound of Formula I, or a pharmaceutically acceptable salt thereof, to a mammal to treat diseases mediated by MMP enzymes preferably, although not necessarily, is accomplished by administering the compound, or the salt thereof, in a pharmaceutical dosage form.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid-form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid-form preparations which are intended to be converted, shortly before use, to liquid-form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 to 1000 mg, preferably 10 to 100 mg according to the particular application and the potency of the active component. The composition can, if desired, also contain other compatible therapeutic agents.

In therapeutic use as agents to inhibit a matrix metalloproteinase enzyme for the treatment of atherosclerotic plaque rupture, aortic aneurysm, heart failure, restenosis, periodontal disease, corneal ulceration, cancer metastasis, tumor angiogenesis, arthritis, or other autoimmune or inflammatory disorders dependent upon breakdown of connective tissue, the compounds utilized in the pharmaceutical method of this invention are administered at a dose that is effective to inhibit the hydrolytic activity of one or more matrix metalloproteinase enzymes. The initial dosage of about 1 mg/kg to about 100 mg/kg daily will be effective. A daily dose range of about 25 mg/kg to about 75 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 mg/kg to about 500 mg/kg, and ideally about 25 mg/kg to about 250 mg/kg, such that it will be an amount which is effective to treat the particular disease being prevented or controlled.

The following examples illustrate typical pharmaceutical compositions provided by the invention.

FORMULATION EXAMPLE 1

Tablet Formulation

| Ingredient | Amount (mg) |
|---|---|
| Compound of Example 3 | 25 |
| Lactose | 50 |
| Corn starch (for mix) | 10 |

37

| Tablet Formulation | |
|---|---|
| Ingredient | Amount (mg) |
| Corn starch (paste) | 10 |
| Magnesium stearate (1%) | 5 |
| Total | 100 |

The benzothiadiazine of Example 3, lactose, and corn starch (for mix) are blended to uniformity. The corn starch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of cancer, atherosclerosis, or arthritis.

FORMULATION EXAMPLE 2

| Preparation for Oral Solution | |
|---|---|
| Ingredient | Amount |
| Compound of Example 1 | 400 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the benzothiadiazine of Example 1 is dissolved therein. The saccharin, sodium benzoate, flavor, and dye are added and dissolved. The volume is adjusted to 100 mL with distilled water. Each milliliter of syrup contains 4 mg of invention compound.

FORMULATION EXAMPLE 3
Parenteral Solution

In a solution of 700 mL of propylene glycol and 200 mL of water for injection is suspended 20 g of the compound of Example 2. After suspension is complete, the pH is adjusted to 6.5 with 1N sodium hydroxide, and the volume is made up to 1000 mL with water for injection. The formulation is sterilized, filled into 5.0-mL ampoules each containing 2.0 mL, and sealed under nitrogen.

As matrix metalloproteinase inhibitors, the compounds of Formula I are useful as agents for the treatment of multiple sclerosis. They are also useful as agents for the treatment of atherosclerotic plaque rupture, restenosis, periodontal disease, corneal ulceration, treatment of burns, decubital ulcers, wound repair, heart failure, cancer metastasis, tumor angiogenesis, arthritis, and other inflammatory disorders dependent upon tissue invasion by leukocytes. The MMP inhibitors of Formula I are especially useful for treating rheumatoid arthritis, osteoarthritis, and congestive heart failure.

It should be appreciated that in all invention embodiments described above or in the claims below, whenever an R group such as, for example, $R^1$, $R^2$, $R^3$, $R^4$, $R^5$, or $R^6$, is used more than once to define an invention compound, each use of the R group is independent of any other use of that same R group or, for that matter, any other R group, unless otherwise specified.

What is claimed is:

1. A compound of Formula I

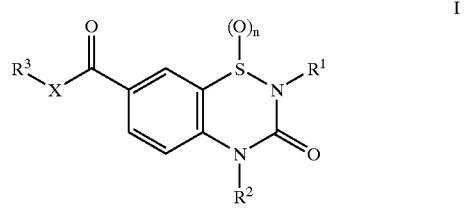

or a pharmaceutically acceptable salt thereof, wherein:

n is 0, 1, or 2;

X is O or NH;

$R^2$ is H, $C_1$–$C_6$ alkyl, or $C_1$–$C_6$ substituted alkyl;

$R^1$ and $R^3$ independently are H, acyl, substituted acyl, $C_1$–$C_6$ alkyl, $C_1$–$C_6$ substituted alkyl, $C_2$–$C_6$ alkenyl, $C_2$–$C_6$ substituted alkenyl, $C_2$–$C_6$ alkynyl, $C_1$–$C_6$ substituted alkynyl, $(CH_2)_m$ aryl, $(CH_2)_m$ substituted aryl, $(CH_2)_m$ heteroaryl, $(CH_2)_m$ substituted heteroaryl, $(CH_2)_m$ cycloalkyl, or $(CH_2)_m$ substituted cycloalkyl; and each m independently is an integer of from 0 to 6, with the proviso that $R^3$ is not $(CH_2)_m$ biphenyl or $(CH_2)_m$ substituted biphenyl and $R^1$ and $R^3$ are not both selected from H and $C_1$–$C_6$ alkyl;

wherein substituted aryl and substituted heteroaryl contain from 1 to 3 substituents independently selected from the group consisting of alkyl, alkoxy, thio, thioalkyl, thioalkoxy, $(CH_2)_mN(R^4)S(O)_2(C_1$–$C_6$ alkyl), $(CH_2)_mS(O)_2NR^4R^5$, $S(O)_2NR^4R^5$, $C(O)NR^4R^5$, $N(H)C(O)NR^4R^5$, $O\text{—}C(O)NR^4R^5$, halo, hydroxy, —$COOR^6$, trifluoromethyl, nitro, amino of the formula —$NR^4R^5$, $C(O)NR^4R^5$, $S(O)C_1$–$C_6$ alkyl, $S(O)_2C_1$–$C_6$ alkyl, 5-membered heteroaryl, $N(R^5)C(O)O(C_1$–$C_6$ alkyl), $T(CH_2)_pQR^4$, $T(CH_2)_pCO_2R^4$, and phenyl, substituted alkyl, substituted alkenyl, substituted alkoxy, and substituted alkynyl contain from 1 to 3 substituents independently selected from $NR^4R^5$, phenyl, substituted phenyl, $(CH_2)_m$—$C(O)$ phenyl, $(CH_2)_mC(O)$ substituted phenyl, $(CH_2)_m$—$S(O)_{0-2}$ phenyl, $(CH_2)_mS(O)_{0-2}$ substituted phenyl, $(CH_2)_m$—$C(O)$ heteroaryl, $(CH_2)_mC(O)$ substituted heteroaryl, $(CH_2)_m$—$S(O)_{0-2}$ heteroaryl, $(CH_2)_m$—$S(O)_{0-2}$ substituted heteroaryl, $(CH_2)_m$ cycloalkyl, heterocycle, thio $C_1$–$C_6$ alkyl, $C_1$–$C_6$ alkoxy, hydroxy, acyl, carboxy, alkanoyl, $C_1$–$C_6$ alkoxycarbonyl, halo, nitro, nitrile, cycloalkyl, and a 5- or 6-membered carbocyclic ring or heterocyclic ring having 1 or 2 heteroatoms selected from nitrogen, substituted nitrogen, oxygen, and sulfur, substituted cycloalkyl contain a substituent hydroxy or keto;

p is 1 to 6,

T is O, S, SO, $SO_2$, $NR^4$, $N(O)R^4$, $NR^4R^6Y$, or $CR^4R^5$,

Q is O, S, SO, $SO_2$, $NR^5$, $N(O)R^5$, or $NR^5R^6Y$,

Y is a counter ion of halo, $R^6$ is H, $C_1$–$C_6$ alkyl, or substituted $C_1$–$C_6$ alkyl, $R^4$ and $R^5$ independently are hydrogen, $C_1$–$C_6$ alkyl, $C_2$–$C_6$ alkenyl, $C_2$–$C_6$ alkynyl, acyl, $(CH_2)_m$ aryl, (CH$_2$)$_m$ heteroaryl, (CH$_2$)$_m$ cycloalkyl, wherein these groups may be unsubstituted or substituted as described herein, or R$^4$ and R$^5$ are taken together with the nitrogen atom to which they are attached to form a 3- to 7-membered ring containing carbon atoms, the nitrogen atom bearing R$^4$ and R$^5$, and optionally 1 or 2 heteroatoms selected from O, S, NH, and NR$^2$, wherein R$^2$ is as defined above, the ring optionally may be substituted with oxo ("=O") on a carbon atom, heterocycle is selected from oxiranyl, pyrrolidinyl, piperidyl, tetrahydropyranyl, and morpholinyl, acyl is C(O)—(C$_1$–C$_6$ alkyl), C(O)-phenyl, or C(O)-naphthyl, aryl is phenyl or naphthyl, and heteroaryl is 5-membered heteroaryl selected from furanyl, pyrrolyl, pyrazolyl, imidazolyl, thiazolyl, thienyl, oxazolyl, isoxazolyl, isothiazolyl, and tetrazolyl, 6-membered heteroaryl selected from pyridyl, or 9-membered heteroaryl selected from benzothienyl, indolyl, benzotriazolyl, indazolyl, benzofuranyl, benzo[1,2,5]oxadiazolyl, (2,1,3) benzothiadiazolyl, and benzisoxazolyl.

2. A compound of Formula II

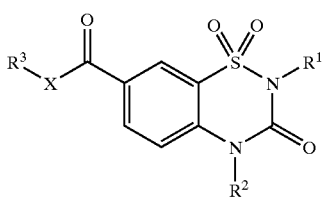

II or a pharmaceutically acceptable salt thereof, wherein:

X is O or NH;

R$^2$ is H, or C$_1$–C$_6$ alkyl, or C$_1$–C$_6$ substituted alkyl;

R$^1$ and R$^3$ independently are H, acyl, substituted acyl, C$_1$–C$_6$ alkyl, C$_1$–C$_6$ substituted alkyl, C$_2$–C$_6$ alkenyl, C$_2$–C$_6$ substituted alkenyl, C$_2$–C$_6$ alkynyl, C$_1$–C$_6$ substituted alkynyl, (CH$_2$)$_m$ aryl, (CH$_2$)$_m$ substituted aryl, (CH$_2$)$_m$ heteroaryl, (CH$_2$)$_m$ substituted heteroaryl, (CH$_2$)$_m$ cycloalkyl, or (CH$_2$)$_m$ substituted cycloalkyl; and each m independently is an integer of from 0 to 6, with the proviso that R$^3$ is not (CH$_2$)$_m$ biphenyl or (CH$_2$)$_m$ substituted biphenyl and R$^1$ and R$^3$ are not both selected from H and C$_1$–C$_6$ alkyl;

wherein substituted aryl and substituted heteroaryl contain from 1 to 3 substituents independently selected from the group consisting of alkyl, alkoxy, thio, thioalkyl, thioalkoxy, (CH$_2$)$_m$N(R$^4$)S(O)$_2$(C$_1$–C$_6$ alkyl), (CH$_2$)$_m$S(O)$_2$NR$^4$R$^5$, S(O)$_2$NR$^4$R$^5$, C(O) NR$^4$R$^5$, N(H)C(O)NR$^4$R$^5$, O—C(O)NR$^4$R$^5$, halo, hydroxy, —COOR$^6$, trifluoromethyl, nitro, amino of the formula —NR$^4$R$^5$, C(O)NR$^4$R$^5$, S(O)C$_1$–C$_6$ alkyl, S(O)$_2$C$_1$–C$_6$ alkyl, 5-membered heteroaryl, N(R$^5$)C(O) O(C$_1$–C$_6$ alkyl), T(CH$_2$)$_p$QR$^4$, T(CH$_2$)$_p$CO$_2$R$^4$, and phenyl, substituted alkyl, substituted alkenyl, substituted alkoxy, and substituted alkynyl contain from 1 to 3 substituents independently selected from NR$^4$R$^5$, phenyl, substituted phenyl, (CH$_2$)$_m$—C(O) phenyl, (CH$_2$)$_m$C(O) substituted phenyl, (CH$_2$)$_m$—S(O)$_{0-2}$ phenyl, (CH$_2$)$_m$S(O)$_{0-2}$ substituted phenyl, (CH$_2$)$_m$—C(O) heteroaryl, (CH$_2$)$_m$C(O) substituted heteroaryl, (CH$_2$)$_m$—S(O)$_{0-2}$ heteroaryl, (CH$_2$)$_m$—S(O)$_{0-2}$ substituted heteroaryl, (CH$_2$)$_m$ cycloalkyl, heterocycle, thio C$_1$–C$_6$ alkyl, C$_1$–C$_6$ alkoxy, hydroxy, acyl, carboxy, alkanoyl, C$_1$–C$_6$ alkoxycarbonyl, halo, nitro, nitrile, cycloalkyl, and a 5- or 6-membered carbocyclic ring or heterocyclic ring having 1 or 2 heteroatoms selected from nitrogen, substituted nitrogen, oxygen, and sulfur, substituted cycloalkyl contain a substituent hydroxy or keto;

p is 1 to 6,

T is O, S, SO, SO$_2$, NR$^4$, N(O)R$^4$, NR$^4$R$^6$Y, or CR$^4$R$^5$,

Q is O, S, SO, SO$_2$, NR$^5$, N(O)R$^5$, or NR$^5$R$^6$Y,

Y is a counter ion of halo,

R$^6$ is H, C$_1$–C$_6$ alkyl, or substituted C$_1$–C$_6$ alkyl,

R$^4$ and R$^5$ independently are hydrogen, C$_1$–C$_6$ alkyl, C$_2$–C$_6$ alkenyl, C$_2$–C$_6$ alkynyl, acyl, (CH$_2$)$_m$ aryl, (CH$_2$)$_m$ heteroaryl, (CH$_2$)$_m$ cycloalkyl, wherein these groups may be unsubstituted or substituted as described herein, or R$^4$ and R$^5$ are taken together with the nitrogen atom to which they are attached to form a 3- to 7-membered ring containing carbon atoms, the nitrogen atom bearing R$^4$ and R$^5$, and optionally 1 or 2 heteroatoms selected from O, S, NH, and NR$^2$, wherein R$^2$ is as defined above, the ring optionally may be substituted with oxo ("=O") on a carbon atom, heterocycle is selected from oxiranyl, pyrrolidinyl, piperidyl, tetrahydropyranyl, and morpholinyl, acyl is C(O)—(C$_1$–C$_6$ alkyl), C(O)-phenyl, or C(O)-naphthyl, aryl is phenyl or naphthyl, and heteroaryl is 5-membered heteroaryl selected from furanyl, pyrrolyl, pyrazolyl, imidazolyl, thiazolyl, thienyl, oxazolyl, isoxazolyl, isothiazolyl, and tetrazolyl, 6-membered heteroaryl selected from pyridyl, or 9-membered heteroaryl selected from benzothienyl, indolyl, benzotriazolyl, indazolyl, benzofuranyl, benzo[1,2,5]oxadiazolyl, (2,1,3) benzothiadiazolyl, and benzisoxazolyl.

3. A pharmaceutical composition, comprising a compound of claim 1, or a pharmaceutically acceptable salt thereof, admixed with a pharmaceutically acceptable carrier, diluent, or excipient.

4. A pharmaceutical composition, comprising a compound of claim 2, or a pharmaceutically acceptable salt thereof, admixed with a pharmaceutically acceptable carrier, diluent, or excipient.

5. A method for treating a osteoarthritis, comprising administering to a patient suffering from such a disease an effective amount of a compound of claim 1, or a pharmaceutically acceptable salt thereof.

6. A compound of Formula I

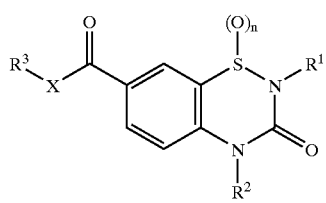

I or a pharmaceutically acceptable salt thereof, wherein:

n is 0, 1, or 2;

X is O or NH;

$R^2$ is H, $C_1$–$C_6$ alkyl, or $C_1$–$C_6$ substituted alkyl;

$R^1$ and $R^3$ independently are H, $C_1$–$C_6$ alkyl, $C_1$–$C_6$ substituted alkyl, $C_2$–$C_6$ alkenyl or $C_2$–$C_6$ substituted alkenyl, $C_2$–$C_6$ alkynyl or $C_1$–$C_6$ substituted alkynyl, $(CH_2)_m$ aryl, $(CH_2)_m$ heteroaryl, or $(CH_2)_m$ cycloalkyl; and m is an integer from 0 to 6;

wherein and $R^1$ and $R^3$ are not both selected from H and $C_1$–$C_6$ alkyl;

wherein substituted aryl and substituted heteroaryl contain from 1 to 3 substituents independently selected from the group consisting of alkyl, alkoxy, thio, thioalkyl, thioalkoxy, $(CH_2)_mN(R^4)S(O)_2(C_1$–$C_6$ alkyl), $(CH_2)_mS(O)_2NR^4R^5$, $S(O)_2NR^4R^5$, $C(O)NR^4R^5$, $N(H)C(O)NR^4R^5$, $O$—$C(O)NR^4R^5$, halo, hydroxy, —$COOR^6$, trifluoromethyl, nitro, amino of the formula —$NR^4R^5$, $C(O)NR^4R^5$, $S(O)C_1$–$C_6$ alkyl, $S(O)_2C_1$–$C_6$ alkyl, 5-membered heteroaryl, $N(R^5)C(O)O(C_1$–$C_6$ alkyl), $T(CH_2)_pQR^4$, $T(CH_2)_pCO_2R^4$, and phenyl, substituted alkyl, substituted alkenyl, substituted alkoxy, and substituted alkynyl contain from 1 to 3 substituents independently selected from $NR^4R^5$, phenyl, substituted phenyl, $(CH_2)_m$—$C(O)$ phenyl, $(CH_2)_mC(O)$ substituted phenyl, $(CH_2)_m$—$S(O)_{0-2}$ phenyl, $(CH_2)_mS(O)_{0-2}$ substituted phenyl, $(CH_2)_m$—$C(O)$ heteroaryl, $(CH_2)_mC(O)$ substituted heteroaryl, $(CH_2)_m$—$S(O)_{0-2}$ heteroaryl, $(CH_2)_m$—$S(O)_{0-2}$ substituted heteroaryl, $(CH_2)_m$ cycloalkyl, heterocycle, thio $C_1$–$C_6$ alkyl, $C_1$–$C_6$ alkoxy, hydroxy, acyl, carboxy, alkanoyl, $C_1$–$C_6$ alkoxycarbonyl, halo, nitro, nitrile, cycloalkyl, and a 5- or 6-membered carbocyclic ring or heterocyclic ring having 1 or 2 heteroatoms selected from nitrogen, substituted nitrogen, oxygen, and sulfur, substituted cycloalkyl contain a substituent hydroxy or keto;

p is 1 to 6,

T is O, S, SO, $SO_2$, $NR^4$, $N(O)R^4$, $NR^4R^6Y$, or $CR^4R^5$,

Q is O, S, SO, $SO_2$, $NR^5$, $N(O)R^5$, or $NR^5R^6Y$,

Y is a counter ion of halo, $R^6$ is H, $C_1$–$C_6$ alkyl, or substituted $C_1$–$C_6$ alkyl, $R^4$ and $R^5$ independently are hydrogen, $C_1$–$C_6$ alkyl, $C_2$–$C_6$ alkenyl, $C_2$–$C_6$ alkynyl, acyl, $(CH_2)_m$ aryl, $(CH_2)_m$ heteroaryl, $(CH_2)_m$ cycloalkyl, wherein these groups may be unsubstituted or substituted as described herein, or $R^4$ and $R^5$ are taken together with the nitrogen atom to which they are attached to form a 3- to 7-membered ring containing carbon atoms, the nitrogen atom bearing $R^4$ and $R^5$, and optionally 1 or 2 heteroatoms selected from O, S, NH, and $NR^2$, wherein $R^2$ is as defined above, the ring optionally may be substituted with oxo ("=O") on a carbon atom, heterocycle is selected from oxiranyl, pyrrolidinyl, piperidyl, tetrahydropyranyl, and morpholinyl, acyl is $C(O)$—$(C_1$–$C_6$ alkyl), $C(O)$-phenyl, or $C(O)$-naphthyl, aryl is phenyl or naphthyl, and heteroaryl is 5-membered heteroaryl selected from furanyl, pyrrolyl, pyrazolyl, imidazolyl, thiazolyl, thienyl, oxazolyl, isoxazolyl, isothiazolyl, and tetrazolyl, 6-membered heteroaryl selected from pyridyl, or 9-membered heteroaryl selected from benzothienyl, indolyl, benzotriazolyl, indazolyl, benzofuranyl, benzo[1,2,5]oxadiazolyl, (2,1,3)benzothiadiazolyl, and benzisoxazolyl.

7. A compound of Formula II

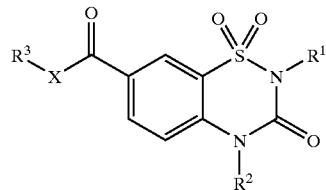

or a pharmaceutically acceptable salt thereof, wherein:

X is O or NH;

$R^2$ is H, or $C_1$–$C_6$ alkyl, or $C_1$–$C_6$ substituted alkyl;

$R^1$ and $R^3$ independently are H, $C_1$–$C_6$ alkyl, $C_1$–$C_6$ substituted alkyl, $C_2$–$C_6$ alkenyl or $C_2$–$C_6$ substituted alkenyl, $C_2$–$C_6$ alkynyl or $C_1$–$C_6$ substituted alkynyl, $(CH_2)_m$ aryl, $(CH_2)_m$ heteroaryl, or $(CH_2)_m$ cycloalkyl; and m is an integer from 0 to 6;

wherein and $R^1$ and $R^3$ are not both selected from H and $C_1$–$C_6$ alkyl;

wherein substituted aryl and substituted heteroaryl contain from 1 to 3 substituents independently selected from the group consisting of alkyl, alkoxy, thio, thioalkyl, thioalkoxy, $(CH_2)_mN(R^4)S(O)_2(C_1$–$C_6$ alkyl), $(CH_2)_mS(O)_2NR^4R^5$, $S(O)_2NR^4R^5$, $C(O)NR^4R^5$, $N(H)C(O)NR^4R^5$, $O$—$C(O)NR^4R^5$, halo, hydroxy, —$COOR^6$, trifluoromethyl, nitro, amino of the formula —$NR^4R^5$, $C(O)NR^4R^5$, $S(O)C_1$–$C_6$ alkyl, $S(O)_2C_1$–$C_6$ alkyl, 5-membered heteroaryl, $N(R^5)C(O)O(C_1$–$C_6$ alkyl), $T(CH_2)_pQR^4$, $T(CH_2)_pCO_2R^4$, and phenyl, substituted alkyl, substituted alkenyl, substituted alkoxy, and substituted alkynyl contain from 1 to 3 substituents independently selected from $NR^4R^5$, phenyl, substituted phenyl, $(CH_2)_m$—$C(O)$ phenyl, $(CH_2)_mC(O)$ substituted phenyl, $(CH_2)_m$—$S(O)_{0-2}$ phenyl, $(CH_2)_mS(O)_{0-2}$ substituted phenyl, $(CH_2)_m$—$C(O)$ heteroaryl, $(CH_2)_mC(O)$ substituted heteroaryl, $(CH_2)_m$—$S(O)_{0-2}$ heteroaryl, $(CH_2)_m$—$S(O)_{0-2}$ substituted heteroaryl, $(CH_2)_m$ cycloalkyl, heterocycle, thio $C_1$–$C_6$ alkyl, $C_1$–$C_6$ alkoxy, hydroxy, acyl, carboxy, alkanoyl, $C_1$–$C_6$ alkoxycarbonyl, halo, nitro, nitrile, cycloalkyl, and a 5- or 6-membered carbocyclic ring or heterocyclic ring having 1 or 2 heteroatoms selected from nitrogen, substituted nitrogen, oxygen, and sulfur, substituted cycloalkyl contain a substituent hydroxy or keto;

p is 1 to 6,

T is O, S, SO, $SO_2$, $NR^4$, $N(O)R^4$, $NR^4R^6Y$, or $CR^4R^5$,

Q is O, S, SO, $SO_2$, $NR^5$, $N(O)R^5$, or $NR^5R^6Y$,

Y is a counter ion of halo, $R^6$ is H, $C_1$–$C_6$ alkyl, or substituted $C_1$–$C_6$ alkyl, $R^4$ and $R^5$ independently are hydrogen, $C_1$–$C_6$ alkyl, $C_2$–$C_6$ alkenyl, $C_2$–$C_6$ alkynyl, acyl, $(CH_2)_m$ aryl, $(CH_2)_m$ heteroaryl, $(CH_2)_m$ cycloalkyl, wherein these groups may be unsubstituted or substituted as described herein, or $R^4$ and $R^5$ are taken together with the nitrogen atom to which they are attached to form a 3- to 7-membered ring containing carbon atoms, the nitrogen atom bearing $R^4$ and $R^5$, and optionally 1 or 2 heteroatoms selected from O, S, NH, and $NR^2$, wherein $R^2$ is as defined above, the ring optionally may be substituted with oxo ("=O") on a carbon atom, heterocycle is selected from oxiranyl, pyrrolidinyl, piperidyl, tetrahydropyranyl, and morpholinyl, acyl is C(O)—(C$_1$–C$_6$ alkyl), C(O)-phenyl, or C(O)-naphthyl, aryl is phenyl or naphthyl, and heteroaryl is 5-membered heteroaryl selected from furanyl, pyrrolyl, pyrazolyl, imidazolyl, thiazolyl, thienyl, oxazolyl, isoxazolyl, isothiazolyl, and tetrazolyl, 6-membered heteroaryl selected from pyridyl, or 9-membered heteroaryl selected from benzothienyl, indolyl, benzotriazolyl, indazolyl, benzofuranyl, benzo[1,2,5]oxadiazolyl, (2,1,3) benzothiadiazolyl, and benzisoxazolyl.

8. A compound selected from the group consisting of:
2-Benzyl-4-methyl-1,1,3-trioxo-1,2,3,4-tetrahydro-1l$^6$-benzo[1,2,4]thiadiazine-7-carboxylic acid benzyl ester;
2-Benzyl-4-methyl-1,1,3-trioxo-1,2,3,4-tetrahydro-1l6-benzo[1,2,4]thiadiazine-7-carboxylic acid benzylamide; and
2-Benzyl-4-methyl-1,1,3-trioxo-1,2,3,4-tetrahydro-1l$^6$-benzo[1,2,4]thiadiazine-7-carboxylic acid (pyridin-4-ylmethyl)-amide.

9. A pharmaceutical composition comprising a compound of claim 6 together with a pharmaceutically acceptable carrier, diluent, or excipient.

10. A pharmaceutical composition comprising a compound of claim 7 together with a pharmaceutically acceptable carrier, diluent, or excipient.

11. A method for treating osteoarthritis comprising administering to a patient having osteoarthritis and in need of treatment an effective amount of a compound of claim 6.

12. A compound selected from the group consisting of:
2-Benzyl-4-methyl-1,1,3-trioxo-1,2,3,4-tetrahydro-1l$^6$-benzo[1,2,4]thiadiazine-7-carboxylic acid 3-methoxy-benzylamide;
4-(7-Benzylcarbamoyl-4-methyl-1,1,3-trioxo-3,4-dihydro-1H-1l$^6$-benzo[1,2,4]thiadiazin-2-ylmethyl)-benzoic acid;
4-[7-(4-Methoxy-benzylcarbamoyl)-4-methyl-1,1,3-trioxo-3,4-dihydro-1H-1l$^6$-benzo[1,2,4]thiadiazin-2-ylmethyl]-benzoic acid;
4-[7-(3-Methoxy-benzylcarbamoyl)-4-methyl-1,1,3-trioxo-3,4-dihydro-1H-1l$^6$-benzo[1,2,4]thiadiazin-2-ylmethyl]-benzoic acid;
{4-[7-(4-Methoxy-benzylcarbamoyl)-4-methyl-1,1,3-trioxo-3,4-dihydro-1H-1l$^6$-benzo[1,2,4]thiadiazin-2-ylmethyl]-phenyl}-acetic acid; and
4-Methyl-2-(4-methylsulfamoyl-benzyl)-1,1,3-trioxo-1,2,3,4-tetrahydro-1l$^6$-benzo[1,2,4]thiadiazine-7-carboxylic acid 4-methoxy-benzylamide.

13. A compound selected from the group consisting of:
2-Benzyl-4-methyl-1,1,3-trioxo-1,2,3,4-tetrahydro-1l$^6$-benzo[1,2,4]thiadiazine-7-carboxylic acid (1H-indol-5-ylmethyl)-amide;
2-Benzyl-4-methyl-1,1,3-trioxo-1,2,3,4-tetrahydro-1l$^6$-benzo[1,2,4]thiadiazine-7-carboxylic acid (1H-indol-5-ylmethyl)-amide;
2-Benzyl-4-methyl-1,1,3-trioxo-1,2,3,4-tetrahydro-1l$^6$-benzo[1,2,4]thiadiazine-7-carboxylic acid 4-fluoro-benzylamide;
4-Methyl-2-(4-nitro-benzyl)-1,1,3-trioxo-1,2,3,4-tetrahydro-1l$^6$-benzo[1,2,4]thiadiazine-7-carboxylic acid 4-methoxy-benzylamide;
4-Methyl-2-[4-(morpholine-4-sulfonyl)-benzyl]-1,1,3-trioxo-1,2,3,4-tetrahydro-1l$^6$-benzo[1,2,4]thiadiazine-7-carboxylic acid 4-methoxy-benzylamide;
4-[7-(4-Fluoro-benzylcarbamoyl)-4-methyl-1,1,3-trioxo-3,4-dihydro-1H-1l$^6$-benzo[1,2,4]thiadiazin-2-ylmethyl]-benzoic acid methyl ester;
2-Benzyl-4-methyl-1,1,3-trioxo-1,2,3,4-tetrahydro-1l$^6$-benzo[1,2,4]thiadiazine-7-carboxylic acid (2-methoxy-pyridin-4-ylmethyl)-amide;
4-Methyl-2-naphthalen-2-ylmethyl-1,1,3-trioxo-1,2,3,4-tetrahydro-1l$^6$-benzo[1,2,4]thiadiazine-7-carboxylic acid 4-methoxy-benzylamide;
2-Benzyl-4-methyl-1,1,3-trioxo-1,2,3,4-tetrahydro-1l$^6$-benzo[1,2,4]thiadiazine-7-carboxylic acid (2,1,3-benzothiadiazol-5-ylmethyl)-amide;
4-[7-(4-Fluoro-benzylcarbamoyl)-4-methyl-1,1,3-trioxo-3,4-dihydro-1H-1l$^6$-benzo[1,2,4]thiadiazin-2-ylmethyl]-benzoic acid;
4-Methyl-1,1,3-trioxo-2-[4-(piperidine-1-carbonyl)-benzyl]-1,2,3,4-tetrahydro-1l$^6$-benzo[1,2,4]thiadiazine-7-carboxylic acid 4-methoxy-benzylamide;
2-{4-[7-(4-Methoxy-benzylcarbamoyl)-4-methyl-1,1,3-trioxo-3,4-dihydro-1H-1l$^6$-benzo[1,2,4]thiadiazin-2-ylmethyl]-benzoylamino}-3-methyl-butyric acid;
2-(4-Cyano-benzyl)-4-methyl-1,1,3-trioxo-1,2,3,4-tetrahydro-1l$^6$-benzo[1,2,4]thiadiazine-7-carboxylic acid 4-methoxy-benzylamide;
4-Methyl-1,1,3-trioxo-2-[4-(2H-tetrazol-5-yl)-benzyl]-1,2,3,4-tetrahydro-1λ$^6$-benzo[1,2,4]thiadiazine-7-carboxylic acid 4-methoxy-benzylamide; and
2-Benzo[1,2,5]oxadiazol-5-ylmethyl-4-methyl-1,1,3-trioxo-1,2,3,4-tetrahydro-1l$^6$-benzo[1,2,4]thiadiazine-7-carboxylic acid 4-methoxy-benzylamide.

14. A compound selected from the group consisting of:
2-Benzyl-4-methyl-1,1,3-trioxo-1,2,3,4-tetrahydro-1l$^6$-benzo[1,2,4]thiadiazine-7-carboxylic acid 4-methoxy-benzylamide;
4-(7-Benzylcarbamoyl-4-methyl-1,1,3-trioxo-3,4-dihydro-1H-1l$^6$-benzo[1,2,4]thiadiazin-2-ylmethyl)-benzoic acid tert-butyl ester;
2-(4-Methanesulfonyl-benzyl)-4-methyl-1,1,3-trioxo-1,2,3,4-tetrahydro-1l$^6$-benzo[1,2,4]thiadiazine-7-carboxylic acid benzylamide; and
2-(4-Methanesulfonyl-benzyl)-4-methyl-1,1,3-trioxo-1,2,3,4-tetrahydro-1l$^6$-benzo[1,2,4]thiadiazine-7-carboxylic acid 4-methoxy-benzylamide.

15. A compound selected from the group consisting of:
2-Benzyl-4-methyl-1,1,3-trioxo-1,2,3,4-tetrahydro-1l$^6$-benzo[1,2,4]thiadiazine-7-carboxylic acid 4-(2-tert-butylsulfamoyl-ethyl)-benzylamide;
2-Benzyl-4-methyl-1,1,3-trioxo-1,2,3,4-tetrahydro-1l$^6$-benzo[1,2,4]thiadiazine-7-carboxylic acid (1H-indol-2-ylmethyl)-amide;
2-Benzyl-4-methyl-1,1,3-trioxo-1,2,3,4-tetrahydro-1l$^6$-benzo[1,2,4]thiadiazine-7-carboxylic acid 4-(2-sulfamoyl-ethyl)-benzylamide;
4-[7-(4-Methoxy-benzylcarbamoyl)-4-methyl-1,1,3-trioxo-3,4-dihydro-1H-1l$^6$-benzo[1,2,4]thiadiazin-2-ylmethyl]-benzoic acid tert-butyl ester;
2-Biphenyl-4-ylmethyl-4-methyl-1,1,3-trioxo-1,2,3,4-tetrahydro-1l$^6$-benzo[1,2,4]thiadiazine-7-carboxylic acid 4-methoxy-benzylamide;
4-[7-(4-Methoxy-benzylcarbamoyl)-4-methyl-1,1,3-trioxo-3,4-dihydro-1H-1l$^6$-benzo[1,2,4]thiadiazin-2-ylmethyl]-benzoic acid 2-dimethylamino-ethyl ester hydrochloride;
2-(4-Amino-benzyl)-4-methyl-1,1,3-trioxo-1,2,3,4-tetrahydro-1λ$^6$-benzo[1,2,4]thiadiazine-7-carboxylic acid 4-methoxy-benzylamide;

4-Methyl-1,1,3-trioxo-2-pent-2-ynyl-1,2,3,4-tetrahydro-11$^6$-benzo[1,2,4]thiadiazine-7-carboxylic acid 4-methoxy-benzylamide;

4-Methyl-1,1,3-trioxo-2-(1-phenyl-ethyl)-1,2,3,4-tetrahydro-11$^6$-benzo[1,2,4]thiadiazine-7-carboxylic acid 4-methoxy-benzylamide; and 2-(5-Cyano-pentyl)-4-methyl-1,1,3-trioxo-1,2,3,4-tetrahydro-11$^6$-benzo[1,2,4]thiadiazine-7-carboxylic acid 4-methoxy-benzylamide.

16. A compound selected from the group consisting of:

2-(E)-But-2-enyl-4-methyl-1,1,3-trioxo-1,2,3,4-tetrahydro-11$^6$-benzo[1,2,4]thiadiazine-7-carboxylic acid 4-methoxy-benzylamide;

4-Methyl-1,1,3-trioxo-2-(E)-pent-2-enyl-1,2,3,4-tetrahydro-11$^6$-benzo[1,2,4]thiadiazine-7-carboxylic acid 4-methoxy-benzylamide;

4-Methyl-2-(2-methyl-allyl)-1,1,3-trioxo-1,2,3,4-tetrahydro-11$^6$-benzo[1,2,4]thiadiazine-7-carboxylic acid 4-methoxy-benzylamide;

4-Methyl-2-(3-methyl-but-2-enyl)-1,1,3-trioxo-1,2,3,4-tetrahydro-11$^6$-benzo[1,2,4]thiadiazine-7-carboxylic acid 4-methoxy-benzylamide;

4-Methyl-1,1,3-trioxo-2-[2-(toluene-4-sulfonyl)-ethyl]-1,2,3,4-tetrahydro-11$^6$-benzo[1,2,4]thiadiazine-7-carboxylic acid 4-methoxy-benzylamide;

2-[3-(4-Fluoro-phenyl)-3-oxo-propyl]-4-methyl-1,1,3-trioxo-1,2,3,4-tetrahydro-11$^6$-benzo[1,2,4]thiadiazine-7-carboxylic acid 4-methoxy-benzylamide;

4-Methyl-1,1,3-trioxo-2-{2-[(1-phenyl-methanoyl)-amino]-ethyl}-1,2,3,4-tetrahydro-11$^6$-benzo[1,2,4]thiadiazine-7-carboxylic acid 4-methoxy-benzylamide;

{5-[7-(4-Methoxy-benzylcarbamoyl)-4-methyl-1,1,3-trioxo-3,4-dihydro-1H-11$^6$-benzo[1,2,4]thiadiazin-2-ylmethyl]-isoxazol-3-yl}-carbamic acid methyl ester; and 4-Methyl-1,1,3-trioxo-2-thiazol-4-ylmethyl-1,2,3,4-tetrahydro-11$^6$-benzo[1,2,4]thiadiazine-7-carboxylic acid 4-methoxy-benzylamide.

\* \* \* \* \*